United States Patent [19]
Young et al.

[11] Patent Number: 5,827,735
[45] Date of Patent: Oct. 27, 1998

[54] PLURIPOTENT MESENCHYMAL STEM CELLS AND METHODS OF USE THEREOF

[75] Inventors: Henry E. Young, Macon, Ga.; Paul A. Lucas, Poughkeepsie, N.Y.

[73] Assignee: MorphoGen Pharmaceuticals, Inc., New York, N.Y.

[21] Appl. No.: 650,420

[22] Filed: May 20, 1996

Related U.S. Application Data

[62] Division of Ser. No. 393,453, Feb. 23, 1995, which is a continuation of Ser. No. 901,860, Jun. 22, 1992, abandoned.

[51] Int. Cl.$^6$ .............................. C12N 5/00; C12N 5/02
[52] U.S. Cl. .......................... 435/325; 435/349; 435/380
[58] Field of Search .................................. 435/349, 329, 435/379, 380, 395, 405, 325

[56] References Cited

U.S. PATENT DOCUMENTS

| | | |
|---|---|---|
| 5,041,138 | 8/1991 | Vacanti et al. . |
| 5,197,985 | 3/1993 | Caplan et al. . |
| 5,226,914 | 7/1993 | Caplan et al. . |
| 5,328,695 | 7/1994 | Lucas et al. . |
| 5,486,359 | 1/1996 | Caplan et al. .......................... 424/93.7 |

OTHER PUBLICATIONS

Quinn, LS et al. Nature. 310:692–694, Feb. 21, 1985.
Young et al. (1992) J. Tiss. Cult. Meth. 14:85–92.
Young et al. (1992) J. Tiss. Cult. Meth. 14:31–36.
Young et al. (1991) J. Tiss. Cult. Meth. 13:275–84.
Young et al. (1989) J. Morphology 201:85–103.
Young et al. (1988) Connective Tissure Res. 17:99–112.
Bauer et al. (1985) Proc. Natl. Acad. Sci. USA 82:4132–6.
Baumann et al. (1986) Geburtsh Frauenheilkd 45:234–6.
Buntrock et al. (1984) Exp. Pathol. 26:247–54.
Carpenter et al. (1979) Annu. Rev. Biochem. 48:193–216.
Cohen et al. (1990) Plastic Surgery, vol. I, General Principles, pp. 732–747.
Connolly et al. (1960) Int. Abstr. Surg. 110:417–31.
Cutroneo et al. (1981) Coll. Relat. Res. 1:557–68.
Cutroneo et al. (1986) The Biology of the Extracellular Matrix, pp. 119–176.
Deuel et al. (1981) Proc. Natl. Acad. Sci. USA 78:4584–7.
Duncan et al. (1984) J. Invest Dermatol. 83:377–84.
Edwards et al. (1958) New Eng. J. Med. 259:224–33, 275–85.
Ehrlich et al. (1984) Soft and Hard Tissue Repair: Biological and Clinical Aspects, pp. 533–553.
Ellis (1971) Surg. Gynec. Obstet. 133:497–511.
Engrav et al. (1989) Ann. Plast. Surg. 23:245–8.
Gabbiani et al. (1971) Experientia 27:549–50.
Gabbiani et al. (1972) Am J. Pathol. 66:131–8.
Gauwerky et al. (1988) Huamn Reprod. 3:327–30.
Gauwerky et al. (1990) Arch. Gynecol. Obstet. 247:161–6.
Golan et al. (1991) Int. J. Fert. 36:317–20.
Gospodarowicz et al. (1986) Cell Differentiation 19:1–17.
Graham et al. (1984) J. Orthop. Res. 1:251–6.
Graham et al. (1984) Soft and Hard Tissue Repair: Biological and Clinical Aspects, pp. 361–79.
Grillo et al. (1959) Proc. Soc. Exp. Biol. Med. 101:268–70.
Grotendorst et al. (1985) J. Clin. Invest. 76:2323–9.
Heldelin et al. (1983) Scand. J. Plast. Reconstr. Surg. 17:179–81.
Hunt et al. (1969) Ann. Surg. 170:633–41.
Hunt et al. (1984) Surgery 96:48–54.
Johnson et al. (1928) Surg. Gyn. Obstet. 45:612–9.
Johnson (1928) N. Eng. J. Med. 199:661–4.
Knighton et al. (1982) Ann. Surg. 196:379–87.
Knighton et al. (1986) Ann. Surg. 204:322–30.
Knighton et al. (1988) Growth Factors and Other Aspects of Wound Healing: Biological and Clinical Impications, pp. 319–329.
Lacey (1935) Ann. Surg. 101:529–35.
Lindenberg et al. (1984) Ann. Chr. Gynaecol. 73:11–3.
Lindenberg et al. (1985) Acta Chir. Scand. 151:525–7.
Luciano et al. (1982) Amer. J. Obstet. Gynecol. 146:88–92.
Martinent et al. (1985) Nature 31:158–60.
Narayanan et al. (1985) Biochem. Biophys. Res. Comm. 131:1028–32.
Oka et al. (1983) J. Clin. Invest. 72:249–59.
Orda et al. (1974) J. Surg. Res. 17:365–74.
Peacock et al. (1990) Plastic Surgery, vol. I General Principles, pp. 161–185.
Pffefer et al. (1980) Fertil. Steril. 33:245–56.
Pierce et al. (1988) J. Exp. Med. 167:974–87.
Postlethwaite et al. (1984) J. Immunol. 132:2470–7.
Richey et al. (1989) Ann. Plast. Surg. 23:159–65.
Rosenbloom et al. (1983) Cell Immunol. 81:192–8.
Ross et al. (1978) Cell 14:203–10.
Ross et al. (1987) Ann. Rev. Med. 38:71–9.
Rudolph et al. (1978) Plast. Reconstr. Surg. 62:185–96.
Russell et al. (1977) J. Cell Physiol. 93:389–94.
Scher et al. (1979) Biochem. Biophys. Acta 560:217–41.
Seppa et al. (1982) J. Cell. Biol. 92:584–8.
Shimokado et al. (1985) 43:277–86.

(List continued on next page.)

*Primary Examiner*—David Saunders
*Attorney, Agent, or Firm*—Klauber & Jackson

[57] ABSTRACT

A scar inhibitory factor protein isolate from mammalian basement membranes is provided that inhibits lineage commitment and differentiation of stem cells in vitro and in vivo. The protein isolate is characterized by its ability to inhibit stem cell commitment to a fibroblastic-scar phenotype without killing the cells, thus allowing their differentiation into normal tissue phenotypes. SIF thus limits the amount of scar tissue formation at the site of delivery, while maximizing the potential for the stem cells to differentiate into other tissue phenotypes (muscle, cartilage, bone, fat, etc.). Therefore, it is useful in treating numerous disorders and injuries that currently result in scar tissue or fibrous adhesion formation. The protein isolate can be administered in various modalities in vivo, i.e., as a transdermal patch, incorporated into wound dressings, incorporated into absorbable suture material, incorporated into a bioerodible polymer matrix by itself or interspersed with differentiation factors near the site of tissue injury, sprayed onto prosthetic implants, and can be administered directly to cells cultured in vitro.

17 Claims, 4 Drawing Sheets

OTHER PUBLICATIONS

Simpson et al. (1972) J. Clin. Invest. 51:2009–23.
Soules et al. (1982) Am. J. Obstet. Gynecol. 143:829–34.
Sporn et al. (1986) Science 233:532–4.
Spencer (1977) Reconstructive Microsurgery, pp. 342–349.
Sprugel et al. (1988) Growth Factors and Other aspects of Wound Healing: Biological and Clinical Implicationsl pp. 77–91.
Staindl et al. (1981) Arch. Otorhinolaryngol. 233:105–66.
Swolin (1966) Acta Obstet. et Gynecol. Scand. 45:473–98.
Topol et al. (1981) Plast. Reconstr. Surg. 68:227–30.
Van Winkle (1967) Surg. Gynecol. Obstet. 125:131–42.
Wahl et al. (1987) Proc. Natl. Acad. Sci. USA 84:5788–92.
Weiss et al. (1944) Proc. Soc. Exp. Biol. 55:77–80.
Williams et al. (1976) Plast. Reconstr. Surg. 57:562–9.
Yaita et al. (1975) Japanese J. Surg. 5:56–63.

PLURIPOTENT MESENCHYMAL STEM CELLS AND METHODS OF USE THEREOF

This Application is a Division of application Ser. No. 08/393,453 filed Feb. 23, 1995, entitled "SCAR INHIBITORY FACTOR AND USE THEREOF," which is a continuation of application Ser. No. 07/901,860, filed Jun. 22, 1992, now abandoned.

BACKGROUND OF THE INVENTION

The present invention relates generally to the healing of wounds, and more particularly, to a composition and method for inhibiting the body's response to form scar tissue at the site of a wound.

Today, wound healing abnormalities, such as keloids, hypertrophic scars, fibrous adhesions, and cirrhosis, rather than infection, are among the greatest causes of human disability, disfigurement, and even death. Far more people suffer and die each year from wound healing abnormalities than are saved by organ transplantation or cancer chemotherapy.

Many findings over the past decade suggest that abnormal wound healing may occur in previously unrecognized, as well as recognized, conditions. Some of these conditions can be improved by therapeutic measures. Other conditions are being defined biochemically and molecularly in order to bring a better understanding towards treatment. Most important, we are now beginning to realize that what was once considered normal and acceptable healing is neither normal nor acceptable. To say that normal tissues separated by a scar represents normal healing is naive (Peacock et al, *Plastic Surgery, Vol 1., General Principles*, pp 161–185 (1990)).

Human beings do not have the ability to regenerate compound organs. Instead, they have only the relatively simple, and often unsatisfactory, substitute of fibrous tissue repair to restore physical continuity. Unfortunately, repair in a general sense is regarded as beneficial, yet the method of restoring integrity with fibrous (collagenous) protein deposition may produce functional and cosmetic complications worse than the original wound. Similarly, the effect of overheating on the function of internal organs may be disastrous. For example, it is not the lye burn of the esophagus or the toxic injury of the liver that is fatal to patients, it is the scar (collagen deposition) that forms during tissue repair which results in dysphagia or fatal hepatic cirrhosis. Postoperative intestinal obstruction, stenosis of the bile ducts, ureter, or fallopian tubes, adhesions around tendons, or a hard breast following silicone prosthesis implantation are all consequences of the reparative process in which contraction and fibrous protein synthesis are not controlled.

Open wounds heal by two mechanisms: contraction and re-epithelialization. In some patients these mechanisms fail and the wounds remain open. This is of considerable emotional, social, physical, and financial expense to the patient. Therefore, methods of improving contraction and re-epithelialization are needed i.e Richey et al *Ann. Plast. Surg.* 23: 159–165 (1989) and Engrav et al *Ann. Plast. Surg.* 23: 245–248 (1989). With the discovery and isolation of growth factors, including PDGF, PDAF, TGF-B, PF-4, bFGF, and EGF,(Richey et al *Ann. Plast. Surg.* 23: 159–165 (1989)), as well as a relatively recent report (Knighton et al *Ann. Surg.* 204: 322–300 (1986)) that a platelet extract promotes wound healing in chronic wounds, there has been a resurgence of interest in the study of induced wound contraction, using growth factor therapy. The regulation of wound repair can be divided into three distinct areas: biochemical activation, cellular activation, and cellular response (Knighton et al *Growth Factors and Other Aspects of Wound Healing: Biological and Clinical Implications*, pp 319–329 (1988)). Biochemical activation involves the transition of mechanical injury into biochemical signals which can be understood by the body. The trigger which starts the cascade in action is Hagemann factor. When injury causes disruption of the microcirculation, plasma comes in contact with tissue proteins and the basement membrane. This contact causes activation of Hagemann factor and circulating platelets. Activated Hagemann factor in turn activates four cascades which amplify the initial response and, in turn, result in cellular activation. The activation and clotting cascade produces fibrin to aid in homeostasis and thrombin which causes maximal release of platelet alpha granules. The complement cascade produces many biologically active molecules with C5a being the most important in wound repair. C5a is a potent chemoattractant for neutrophils and monocytes. The kinin cascade results in the production of bradykinin which causes microvascular vasodilation at the wound periphery, and the activation of plasminogen products which result from the enzymatic breakdown of fibrin are themselves biologically active molecules which can cause monocyte migration and vasodilation.

The biological amplification stage results in the influx of cells into the newly created wound. The initial cellular response to wounding involves neutrophils, monocytes, and platelets. Neutrophils are the main debriding cells in the wound response. They have no known regulatory activity but provide the main host defense activity in the wound. Platelets accumulate at the wound site in response to thrombin, platelets release their alpha granules which contain locally acting growth factors. These growth factors signal the local mesenchymal cells and epidermal cells to move, signal their division, and signal the mesenchymal cells to differentiate into fibroblasts and to increase their synthesis of collagen and glycosaminoglycans. This initial release of growth factors by the platelets is thought to be the initiator of the actual repairative response. Following the neutrophils into the newly created wound are the monocytes, which then become wound macrophages. These cells perform many functions in the wound. They assist the neutrophils in host defense and produce many of the same growth factors which are initially released by the platelet. In particular, they are thought to be the source of locally acting growth factors which direct repair until the wound is healed.

The process of healing surface wounds includes re-epithelialization, neovascularization, granulation tissue development, collagen elaboration, maturation and remodeling of the scar, and contraction (Peacock et al *Wound Repair*, pp. 161–815 (1990)). During the early phases of repair, the local accumulation of collagen strongly correlates with the accretion of tensile strength, (Edwards et al *New Engl. J. Med.* 259: 224–233 (1958a) and 259: 275–285 (1958b)), hence measuring collagen content, collagen concentration, and tensile strength at the repair site permits an estimate of the rate of healing.

The major biologic phenomena of surface wound healing will be discussed as separate entities, i.e. epithelialization, contraction, structure and synthesis of fibrous protein and matrix, collagen remodeling, factors affecting collagen metabolism, pharmacological agents, changes in physical properties of collagen.

I. Epithelialization

The major function of the epithelium is to act as a selective barrier between the body and the external environment. The epithelial barrier in humans prevents bacteria, toxic materials, and some radiation from gaining access to the body. It also reduces the loss of fluids, electrolytes, and other substances to the external environment. In general, the epithelium acts as a primary defense against a hostile environment and is a major factor in maintaining internal homeostasis.

Epithelialization alone is sufficient only to provide total healing in partial-thickness wounds such as split-thickness skin graft donor sites and first and second degree burns. Healing of deep dermal injuries may even occur when there has been destruction of the epidermal basal layer, provided that hair follicles, sebaceous and sweat glands remain viable. These structures turn into virtual epithelial production factories manufacturing cells that will migrate to cover the deep partial-thickness injury. Unfortunately, the resulting "skin" is often devoid of hair follicles, sebaceous and sweat glands and, therefore, the "healed skin" is prone to infection. If any type of full-thickness wound is allowed to "heal" by epithelialization only, it is doomed to failure (Peacock et al, *Plastic Surgery, Vol. 1, General Principles*, pp. 161–815 (1990). The epithelium is mainly composed of water, and a body area covered only by epithelium has little, if any, resistance to mechanical disruption.

II. Contraction

It is important to distinguish between contraction and contracture. Contraction is the active biological process that decreases the dimension of the involved connective tissue. Contracture is the end result of the process of contraction. In large, open, full thickness wounds left to heal without skin replacement, this phenomenon may be the salvation of the patient and the surgeon alike.

Although many investigators have made observations on the etiology of contraction over the past 30 years, the cause and control has been elusive. Early observations (Watts et al, *Ann. Surg.*, 148: 153 (1958) and Grillo et al, *Proc. Soc. Exp. Biol. Med.*, 101: 268 (1959) suggested that the contraction process occurred beneath the advancing skin margin. Other studies indicated that the contractile forces originated in the central granulation tissue (W. Van Winkle *Surg. Gynecol. Obstet.*, 125: 131 (1967)). A major advance in understanding wound contraction occurred with the discovery of a specialized form of mesenchymal cell called the myofibroblast (Gabbiani et al, *Experientia,* 27: 549 (1971)). This cell is a typical fibroblast with a well-developed endoplasmic reticulum that also possesses many features of a smooth muscle cell, i.e. massive bundles of intracytoplasmic microfilaments, positive immunofluorescent labeling with anti-human smooth muscle serum, nuclear indentation indicative of contraction, and cell to stroma connections necessary for cellular contractions to be imparted to the whole tissue. While absent in non-traumatized tissues, myofibroblasts have been identified in virtually every tissue undergoing active contraction, including granulation tissue, tendon sheath, and palmar fascia in patients with Dupuytren's (contracture) disease, (Gabbiana et al, *Am. J. Pathol.,* 66: 131, (1972)) and in capsules around breast implants (Rudolph et al, *Plast. Reconstr. Surg.* 62: 185, (1978)). It has been hypothesized that myofibroblasts initiate the contraction process.

However, there may be reason to question the hypothesis that the myofibroblast is the engine of contraction. For example, some observers have noted that the quantity of myofibroblast cells is greater in the tissue after contracture has been completed (Rudolph et al, *Plast. Reconstr. Surg.* 62: 185, (1978)), suggesting that myofibroblasts may not be the initiators of the process. In addition, (Ehrlich, *Soft and Hard Tissue Repair: Biological and Clinical Aspects*, Chap. 28 (1984)) one study demonstrated that although the fibroblast provides the force for contraction, the connective tissue matrix present within the area of tissue repair also plays an important role in the contractile process. One can conclude that, although the active process of contraction is not altered by inhibiting collagen synthesis or deposition, collagen provides the strength and integrity to maintain contracture once it has occurred.

III. Structure and Synthesis of Fibrous Protein and Matrix

Scar tissue collagen may produce success or failure for the surgeon. If insufficient scar tissue is deposited, morbidity and even mortality can result from failure of structural integrity to be reestablished. In contrast, excessive scar formation is more often the bane of the plastic surgeon and other practitioners alike. The major component of scar tissue is the fibrous protein, collagen.

Collagen is a large macromolecule, 300 nm in length, 15 nm in width, with a molecular weight of approximately 300,000. It is composed of three coiled polypetide chains (Miller, *Ann. N.Y. Acad. Sci.,* 460: 1 (1985)) resulting from over 18 gene products arranged into at least 12 distinct types of collagen. Type I collagen, making up about 80% of the collagen in skin has two similar chains both called alpha-1 chains, and a third chain that is slightly dissimilar called an alpha-2 chain. The primary structure carries an amino acid sequence in the form of a tripeptide: Glycine-X-Y, with glycine occurring as every third residue. Hydroxyproline and hydroxylysine occur almost exclusively in collagen.

Collagen can be synthesized by a variety of cell types, but clearly the most important is the fibroblast. Fibroblasts are derived from specialized stem cells normally found in the adventitia of small blood vessels (Grillo, *Ann. Surg.*, 157: 453 (1963)). Although a normally spindle- or stellate-shaped cell, the fibroblast can assume any shape. When actively producing collagen, the fibroblast is characterized by rows of rough endoplasmic reticulum (RER), the site of collagen synthesis (Ross *Biol. Rev.,* 43: 51 (1968)).

Following hydroxylation of proline and lysine, various sugar moieties are added to the molecule to assist in intermolecular crosslinking. The collagen molecule that is secreted from the cell is referred to as the procollagen molecule.

This molecule has large polypeptide chains attached to both its amino and carboxy terminal ends that must be cleaved by specific peptidases before intermolecular bonding can occur. After the amino and carboxy terminal peptides have been removed, the molecule is termed collagen. Each alpha chain contains approximately 1000 amino acids. The tertiary structure is produced by twisting of three alpha chains into a right-handed super helix. The tertiary structure is stabilized by formation of various intramolecular crosslinks, i.e., hydrogen bonds, covalent bonds, and oppositely charged electrostatic groups, resulting in a rigid, rod-like molecule. The primary collagen molecules crosslink with each other to form the fibrils and fibers that provide tensile strength. The molecules are aligned in a characteristic quarter-stagger overlay between molecules producing the 64 nm repeating periodicity.

Unidentified factors control the physical weave of the collagen fibrils and fibers to produce connective tissue scars of varying proportions and physical characteristics. Although many factors contribute to the final strength, elasticity, size, and shape of the scar, the physical weave is probably extremely important. Collagen is not just one molecule, there are multiple genetic types of collagen and each type appears to be associated with a specific function or tissue type.

Fibronectin is another high molecular weight extracellular glycoprotein (Ruoslahti et al, *Coll. Relat. Res.*, 1: 95 (1981)) that is important in tissue repair. It appears early at the wound site in association with fibrin, and its function is to facilitate adhesion, migration, and phagocytic processes of the leucocytes (Grinnell, *J. Cell Biochem.*, 26: 107 (1984)). Fibronectin also provides a primary substrate for the organization and deposition of collagen and matrix by the fibroblasts.

IV. Remodeling of Collagen

Degradation of collagen is as important as collagen production. In normal tissue repair, collagen synthesis and collagen degradation are in a finely controlled state of equilibrium. Loss of this equilibrium results in abnormal tissue repair. The loss of equilibrium may be due to alterations in collagen degradation as well as collagen synthesis. Lack of collagen degradation can result in excessive deposition, i.e., keloid, hypertrophic scar, or hepatic fibrosis. Excessive degradation can result in failure to heal or disruption of repaired wounds. One study (Grillo et al, *J. Cell. Biol.*, 23: 39A (1964)) identified and measured the activity of collagenases to depolymerize collagen. Another study (Peacock 1967) noted the presence of collagenase in a wide variety of human tissues. Since then, collagenase activity has been noted in almost every tissue (Harris et al *N. Engl. J. Med.*, 291: 557 (1974)). Rather than a single enzyme, there are a variety of collagenases, made by many cell types, and they appear to have specific functions under set conditions (Werb *Collagen in health and Disease*, pp. 21 (1982)).

It is important to note that collagen synthesis has nothing to do with the gain in wound tensile strength. Tensile strength results from collagen crosslinking rather than collagen synthesis per se. Moreover, although there is a dramatic increase in wound tensile strength between the third and eighth week, wound strength never reaches that of normal skin (Peacock et al, *Plastic Surgery, Vol. 1, General Principles*, pp. 161–185 (1990)).

V. Factors Affecting Collagen Metabolism

Five systems are activated by tissue injury, and influence collagen metabolism and ultimately the events of wound healing. These systems include vascular changes, hemocoagulation, inflammation, growth factors, and wound environment.

1. Vascular changes

Vascular changes are the first events following tissue injury and consist of a brief period of vasoconstriction followed by vasodilation and leakage of plasma components around the endothelial cells. These events are modulated by the local release and interplay of histamine, bradykinin, prostaglandins (PGE-1, PGE-2, PGA-2), as well as leukotrienes (Sedwick et al, *Handbook of Inflammation*, pp. 27 (1985)). These mediators not only affect endothelial cell capillary leak but also influence mesenchymal cells. For example, histamine appears to stimulate fibroblast proliferation (Russell et al *J. Cell. Physiol.*, 93: 389 (1977) and Topol et al *Plast. Reconstr. Surg.*, 68: 227 (1981)).

2. Hemocoagulation

Hemocoagulation occurs almost synchronously with the vascular changes. Fibrin formed during coagulation controls bleeding and serves as a surface for adherence and degranulation of platelets, as well as a lattice for fibroblast migration (Graham et al, *J. Orthop. Res.*, 1: 251 (1984a) and Graham et al, *Soft and Hard Tissue Repair: Biological and Clinical Aspects*, pp. 361–379 (1984b)). As platelets degranulate, they release platelet-derived growth factor (PDGF) which modulates cell proliferation (Ross et al, *Cell.*, 14: 203 (1978) and Scher et al, *Biochem. Biophys. Acta.*, 560: 217 (1979)).

In addition, PDGF directs fibroblast chemotaxis (Seppa et al, *J. Cel. Biol*, 92: 584- (1982)) and enhances fibroblast collagenase activity (Bauer et al, *Proc. Natl. Acad. Sci. USA*, 82: 4132 (1985)). The coagulation cascade is most important in modulating the cellular events of inflammation and wound healing.

3. Inflammation

Inflammatory cells initially at the wound site are the same as those found in the peripheral blood. True migration of inflammatory cells begins within hours, when polymorphonuclear (PMN) cells make up the majority of inflammatory cells at the site of tissue injury (Simpson et al, *J. Clin. Invest.*, 51: 2009 (1972)). Several locally released compounds are responsible for PMN migration. These include leukotriene $B_4$ (Bray et al, *Prostaglandins*, 22: 213 (1091)), a product of the lipoxygenase pathway of arachidonic acid as well as the $C_{5a}$ portion of complement (Wiggins et al, *J. Exp. Med.*, 153: 1391 (1981)). Such attractants produce a chemical gradient through which the PMNs migrate to localize at a site where damaged tissue digestion and bacterial digestion can be accomplished by the PMNs. While PMNs are not required for subsequent events in collagen metabolism (Simpson et al, *J. Clin. Invest.*, 51: 2009 (1972)), they are important in the defense against infection and, hence, wound healing in general.

The macrophage arrives at the site of tissue trauma 24 to 36 hours after injury and is a key inflammatory cell in modulating wound healing (Leibovich et al, *Am. J. Pathol.*, 78: 71 (1975)). Macrophages are derived from circulating monocytes attracted to the wound site by specific chemoactive agents such as lymphocyte-derived chemotactic factor (Altman et al, *J. Immunol.*, 110"801 (1973)), N-formylmethionyleucylphenylalanine (FMLP) (Schiffman et al, *Proc. Natl. Acad. Sci. USA*, 75: 1059 (1975)), and collagen fragments. Attracted monocytes that have ingested debris are transformed into macrophages, and local macrophages are also recruited. Macrophages secrete a host of biological active products affecting many other cell types. They produce a PDGF-like factor (Shimokado et al, *Cell*, 43: 277–286 (1985) and Martinent et al, *Nature*, 31(;158 (1986)), release material that inhibits collagen synthesis at a transcriptional level (Narayanan et al, *Biochem. Biophys. Res. Commun.*, 131: 1028 (1985)), and are also capable of synthesizing collagen (Lindblad et al, *J. Histochem. Cytochem*, (submitted) (1988)) and fibronectin. And there are reports that the concentration of macrophage products can modulate fibroblast proliferation (Leibovich et al, *Am. J. Pathol.*, 78: 71 (1975) and Diegelmann et al, *Proc. Soc. Exp. Biol. Med.*, 169: 445 (1982)).

Lymphocytes (T and B) are the final inflammatory cell type to populate the wound. The lymphokines that the T-cell releases may inhibit or stimulate collagen synthesis, and stimulate PDGF secretion and macrophage collagenase production (Rosembloom et al, *Cell. Immunol.*, 81: 192 (1983); Duncan et al, *J. Invest. Dermatol.*, 83: 377 (1984) and Postlethwaite et al, *J. Immunol.*, 132: 2470 (1984)).

4. Growth Factors

Growth factors have been discussed throughout this section, but are so important that they require special emphasis. Six locally acting growth factors are presently thought to contribute to wound repair. These are 1) platelet-derived growth factor, 2) platelet-derived angiogenesis factor, 3) transforming growth factor beta, 4) platelet factor 4, 5) basic fibroblast growth factor, and 6) platelet-derived epidermal growth factor.

Platelet-derived growth factor (PDGF) is a mitogen and chemoattractant for fibroblasts (Seppa et al, *J. Cell. Biol.*, 92: 584- (1982); Senior et al, *J. Cell. Biol.,* 96: 382-)1983); (Ross, *Ann. Rev. Med.,* 38: 71–70 (1987); and Pierce et al, *J. Exp. Med.,* 167: 974- (1988)) and smooth muscle cells (Grotendorst et al, *Proc. Natl. Acad. Sci. USA,* 78: 3669- (1981); Grotendorst et al, *J. Cell. Physiol.,* 113: 261- (1982); and Ross, *Ann. Rev. Med.,* 38: 71–79 (1987)). At very low concentrations (0.5–1.0 ng/ml) it causes fibroblast migration and at slightly higher concentrations (2–5 ng/ml) it causes fibroblast mitosis. In animal studies, PDGF has been shown to be a potent stimulator of granulation tissue formation (Sprugel et al, *Growth Factors and Other Aspects of Wound Healing: Biological and Clinical Implications*, pp. 77–91 (1988)). Another study (Grotendorst et al, *J. Clin. Invest.,* 76: 2323–2329 (1985)) demonstrated that PDGF stimulates migration of connective tissue cells, a marked increase in DNA synthesis, and a greater collagen deposition within the first two weeks after implantation. Previous evidence (Kohler et al, *Exp. Cell. Res.,* 87: 297- (1974)) also suggests that PDGF is actually a family of proteins. The parent human product consists of two chains, the A chain and the B chain (Johnson et al, *Embo J.,* 3: 921- (1984)) and is known to be chemotactic and mitogenic for monocytes (Deuel et al, *J. Clin. Invest.,* 69: 1046- (1982); and Pierce et al, *J. Exp. Med.,* 167: 974- (1988)). One study, Pierce et al, *J. Exp. Med.,* 167: 974- (1988)), has shown that rPDGF-BB (recombinant PDGF B-chain homodimer) increases the breaking strength of incisional wounds in rats, while another (Engrav et al, *Ann. Plast. Surg.,* 23: 245–248 (1989)) has shown that rPDGF-BB stimulates wound contraction in normal animals.

Platelet-derived angiogenic factor (PDAF) is a nonmitogenic chemoattractant for capillary endothelial cells which is recovered from thrombin-released platelets (Knighton et al, *Ann. Surg.,* 196: 379–388 (1982)). Its identity is presently not known. It produces a dose dependent capillary endothelial cell migration and inflammation-free angiogenesis in the rabbit corneal assay. Macrophages also produce a similar factor as PDAF (Hunt et al, *Surgery,* 96: 48–54 (1984)).

Transforming growth factor-beta (TGF-B) is released from platelet alpha granules and has many known functions. It is a very potent chemoattractant for monocytes (Wahl et al, *Proc. Natl. Acad. Sci. USA* 84: 5788–5792 (1987)), it inhibits endothelial cell mitosis and at certain concentrations it inhibits fibroblast mitosis, and stimulates collagen and glycosaminoglycan synthesis by fibroblasts (Sporn et al, *Science,* 233: 532–534 (1986)). It also has been shown (Sprugel et al, *Growth Factors and Other Aspects of Wound Healing: Biological and Clinical Implications,* pp. 77–91 (1988)) that TGF-b is a potent stimulator of granulation tissue formation in vivo.

Platelet factor 4 (PF-4) is a chemoattractant for neutrophils which may be partially responsible for the initial influx of neutrophils into the wound space (Deuel et al, *Proc. Natl. Acad. Sci.,* USA 78: 4584–4587 (1981)).

Basic fibroblast growth factor (b-FGF) stimulates the proliferation of capillary endothelial cells, vascular smooth muscle cells, fibroblasts, chondrocytes, myoblasts, etc. (Gospodarowicz et al, *Cell Differentiation,* 19: 1–17 (1986)). FGF also increases the formation of granulation tissue in vivo (Buntrock et al, *Exp. Pathol,* 21: 46–53 (1982a); Buntrock et al, *Exp. Pathol.,* 21: 626067 (1982b); Davidson et al, *J. Cell. Biol.,* 100: 1219–1227 (1985); and Sprugel et al, *Growth Factors and Other Aspects of Wound Healing: Biological and Clinical Implications,* pop. 77–91 (1988)).

Platelet-derived epidermal growth factor (PDEGF) causes migration and mitosis of epidermal cells with very similar biological activity to salivary gland EGF (Oka et al, *J. Clin. Invest.,* 72: 249–259 (1983)). EGF stimulates proliferation of skin and corneal epithelia in organ culture, proliferation and differentiation of epidermis and corneal epithelial cell in vivo (Carpenter et al, *Annu. Rev. Biochem.,* 48: 193–216 (1979)), neoangiogenesis in the rabbit cornea (Gospodarowicz et al, *Cell Differentiation,* 19: 1–17 (1986)), and synthesis of DNA, RNA, protein and hyaluronate in various cell lines in culture (Carpenter et al, *Ann. Rev. Biochem,* 48: 193–216 (1979)). Many cell types, including dermal fibroblasts, possess EGF surface receptors and will proliferate in response to EGF in cell culture (Carpenter et al, *Annu. Rev. Biochem,* 48: 193–216 (1979)).

5. Wound Environment

Wound environment includes factors already discussed as well as additional factors. For example, oxygen tension within the wound (Hunt et al, Surg. Gynecol. Obstet., 135: 561 (1972) and *Surgery,* 90: 262)1981)), is important since transient low wound tissue oxygen seems to stimulate cell migration, balanced synthesis of angiogenic factor and thus collagenase production. Similarly, high lactate levels, the result of hypoxia, stimulate the macrophage to produce angiogenesis factor (Banda et al, *Proc. Natl. Acad. Sci. USA,* 79: 7773 (1982)). In addition a moderate hyperoxic environment can actually increase the rate of open wound closure, probably as a result of increased epidermal activity rather than stimulation of wound contraction (Niinikoski *Clin. Plast. Surg.,* 4: 361 (1977)). There is a need to maintain normal $PO_2$ in the wound environment if healing is to proceed normally (Hunt et al, *Surg. Gynecol. Obstet.,* 135: 561 (1972); Hunt et al, *Am. J. Surg.,* 135: 328 (1978); and Knighton et al, *Surgery,* 90: 262 (1981). Moreover, such studies have stressed that arterial $PO_2$ may not be a reflection of wound tissue $PO_2$ and that, for example, decreased blood volume alone may result in low wound tissue $PO_2$ in spite of normal arterial $PO_2$.

VI. Pharmacologic Agents

1. Corticosteriods

In spite of a vast literature, it is not totally clear how corticosteroids inhibit wound healing (Peacock et al, *Plastic Surgery, Vol.* 1, *General Principles,* pp. 161–185 (1990)). Corticosteroids inhibit fibroblast migration into the wound if an animal has been pretreated (Hunt et al, *Ann. Surg.,* 170: 633 (1969)) and can inhibit propyl hydroxylase activity (Cutroneo et al, *Coll. Relat. Res.,* 1: 557 (1981) and Cutroneo et al, *The Biology of the Extracellular Matrix,* pp. 119–176 (1986)). Although corticosteroids inhibit this enzyme, they do not necessarily prevent collagen deposition.

In addition, there is some speculation that corticosteroids increase collagenolytic activity (Houck et al, *Biochem. Pharmacol.,* 17: 2081 (1968)). Vitamin A appears to reverse the retardation of healing associated with corticosteroids (Hunt et al, *Ann. Surg.,* 170: 633 (1969); Stein et al, *J. Surg. Res.,* 11: 277 (1971); and Ehrlich et al, *Ann. Surg.,* 177: 222 (1973)). Although the reason is unclear, vitamin A reverses the propyl hydroxylation suppression of corticosteroids and is a cell membrane labilizer, while corticosteroids are a membrane stabilizer (Peacock et al, *Plastic Surgery, Vol.* 1, *General Principles,* pp. 161–185 (1990)).

VII. Abnormal Scar Formation

The biochemical processes of wound repair normally culminate in fine-line scars as the only evidence of dermal injury. In certain individuals, however, the repair process may go awry and wounds may heal with large, raised collagenous scars known as keloids or hypertrophic scars. Both lesions have the annoying clinical symptoms of itching, tenderness and pain. Although keloids and hypertrophic scars are characterized by excessive collagen deposition, the causes remain obscure. The clinical course and physical appearance define keloid and hypertrophic scar as separate entities. Keloids frequently persist at the site of injury, often recur after excision, and always overgrow the boundaries of the original wound. In contrast, hypertrophic scars, although often raised and red, remain within the confines of the original wound and tend to regress over an extended period of time, but frequently recur after excision and closure.

The complications of these abnormal scar formations are often severe and their clinical management is frustrating. Both surgeon and patient must accept the reality that neither pharmacologic intervention nor technical skill will ensure prevention or cure. Potential control of abnormal scar formation is thus of paramount interest to the plastic surgeon (Cohen et al, *Plastic Surgery, Vol* 1. *General Principles*, pp 732–747 (1990)).

1. Etiologies of Abnormal Scar Formation

For unknown reasons, keloid and hypertrophic scar formation is unique to man. Attempts to develop animal models for abnormal scar formation have always proved unsuccessful. Despite numerous studies, there is no current theory or explanation to indicate which factor(s) initiate keloid or hypertrophic scar formation.

For example, although the increased incidence of keloids and hypertrophic scars in dark skinned races has been documented in several studies, the lesions are found in all races and populations. Proposed causes of abnormal scar formation have included foreign body reaction, bacterial infection, or the possibility that degraded or denatured collagen serves as the catalyst for scar hyperplasia. None of these theories is supported by reproducible data. The genetic patterns of patients with keloids have not been elucidated clearly. HLA types seem to be unrelated in contrast to the work of others. However, family members are commonly afflicted.

The role of the immune system in scar formation is unclear. Initial studies showed increased IgG in keloid tissue compared with normal dermis. This suggested immune system involvement in keloid pathogenesis. However, subsequent detailed studies of other immunologic parameters, such as serum IgG, and Clq complement component, immune lymphocyte characteristics, and specific tissue immunoglobulins, failed to demonstrate cellular systemic, or local immunologic factor(s) in keloid formers associated with abnormal scar etiology. In addition, there appears to be no correlation between histocompatibility antigens (HLA typing) and keloid formation, as occurs in some immune associated disease states. Moreover, no known circulating stimulatory factor, immune or otherwise, that could account for excessive collagen production in keloids, has been documented.

Other possible causes of keloid formation include thyroid hormone alterations, ingrown hairs, and melanocyte stimulating hormones. Again though, none of the above hypotheses have ever been validated.

One study compared the microvasculature of hypertrophic scars and keloids with that of normal dermis and normal scar. Increased occlusion of the microvessels by endothelial cell proliferation in abnormal scars was observed when compared with normal dermis. That study suggested that perivascular myofibroblast contraction may contribute significantly to increased microvascular occlusion—and resulting hypoxia—in hypertrophic scars and keloids. Myofibroblasts have been found in both keloids and hypertrophic scars, although their role in abnormal scar formation remains obscure. If hypoxia is a major factor contributing to excessive collagen deposition in abnormal scars, the findings noted above may explain how hypoxia is established and how it persists in abnormal wounds.

The hypothesis that hypoxia may significantly influence abnormal scar formation is reasonable, since (Hunt et al, *Am. J. Surg.*, 135: 328 (1978)) the modulating effects of hypoxia on collagen production have been demonstrated. It has been hypothesized that normal endothelial cell proliferation, probably stimulated by fibrin and thrombin during early wound repair, is prolonged or exaggerated in abnormal scar formation. According to that hypothesis, it was suggested that subsequent microvascular occlusion, owing to epithelial hyperplasia and myofibroblast contraction, may stimulate excessive collagen production in keloids and hypertrophic scars. While the theory needs further study, it appears plausible in view of the histologic findings. For example, preliminary fibroblast tissue culture studies (Cohen et al, *Plastic Surgery, Vol.* 1, *General Principles*, pp. 732–747 (1990)) suggest that hypoxia may select a homogenous fibroblast population that produces collagen at a rate significantly greater than that of a heterogenous population of fibroblasts.

2. Biochemical Observations

Early biochemical studies of keloids and hypertrophic scars focused on quantitating enzyme levels and the degree of cellularity in the lesions. Various glycogenic-related enzymes, such as lactic dehydrogenase, were found in increased concentration in keloid compared with normal skin. The collagen-related enzyme, propyl hydroxylase, was also reported to be elevated in keloid compared with normal skin. Propyl hydroxylase is required for the hydroxylation of proline during collagen biosynthesis, and this finding suggested that collagen overproduction was the characteristic abnormality of keloid lesions.

It is possible that the biochemical defect responsible for abnormal scar formation is expressed early in the course of wound repair and cannot be detected by the time abnormal lesions are fully developed. Unfortunately, there are no studies on the early formation of keloids to test such a hypothesis. However, collagen production is elevated in keloid biopsies, and in cultured fibroblasts derived from keloids (Diegelmann et al, *Proc. Soc. Exp. Biol. Med.*, 169: 445 (1982)). Moreover, increased collagen production by cultured fibroblasts derived from keloids persists throughout their in vitro life span. It appears that once keloid fibroblasts responsible for keloids overcome entropy, they do not revert to normal even after being removed from the lesions and placed in culture. No significant differences in DNA content or cellularity were observed in keloids compared with normal dermis, although that matter is still debated. These data suggest that each fibroblast within a keloid is producing excessive collagen, as opposed to an increased number of fibroblasts each producing a normal amount of collagen.

Reasons have been proposed (Cohen et al, *Plastic Surgery, Vol.* 1, *General Principles*, pp. 732–747 (1990)) as to why excessive collagen production occurs and persists in abnormal scars as well as in the fibroblasts derived from those lesions. As mentioned, it may be that excessive collagen producing fibroblasts are selected by the wound environment and that this selection results in excessive collagen production and deposition by fibroblasts in the lesions. This hypothesis is supported by several studies. In one such study (Hunt et al, *Am. J. Surg.*, 135: 328 (1978)) it was reported that increased hypoxia was noted in early animal wounds and that hypoxia stimulates macrophages, in turn, to stimulate fibroblast collagen production. There is reason to believe that keloids are hypoxic, because microvascular occlusion is frequent and some portions of keloids are relatively avascular. Moreover, increased lactate, increased histamine and decreased pH (Cohen et al, *Plastic Surgery, Vol. 1, General Principles*, pp. 732–747 (1990)) are characteristics of abnormal scars that conceivably could create a "stressed" environment selecting fibroblasts that are high collagen producers.

The hypoxic-selectivity hypothesis is substantiated by several reports demonstrating that heterogenous populations of fibroblasts with particular biochemical characteristics can be isolated from normal tissue. Perhaps certain kinds of fibroblasts predominate in abnormal wounds and either (1) fail to respond to regulatory signals ending increased collagen production during early wound healing or (2) are selected and proliferate more abundantly in the "stress" environment of the early wound. There is evidence that keloid-derived fibroblasts, which can be isolated in vivo, are a selected subset of normal dermal fibroblasts that occur more abundantly in abnormal scars. For example, fibroblasts grown out of keloid tissue produce increased extracellular matrix components in vitro (Diegelmann et al, *Proc. Soc. Exp. Biol. Med.*, 169: 445 (1982)), and demonstrate a differential response to hydrocortisone and histamine (Russell et al, *J. Cell. Physiol.*, 93: 389 (1977) and Topol et al, *Plast. Reconstr. Surg.*, 68: 227 (1981)) compared with normal fibroblasts. Recent studies have shown that keloid-derived fibroblasts have reduced growth factor requirements. Such studies indicate that the "type" of fibroblast in abnormal scars is different from fibroblasts in normal dermis. However, such "abnormal" cells are morphologically identical to normal fibroblasts and grow at the same rate (Diegelmann et al, *Proc. Soc. Exp. Biol. Med.*, 169: 445 (1982)).

It is also important to consider the possibility that keloids and hypertrophic scars may result not only from increased collagen production, but also from decreased collagen degradation. There is biochemical evidence for an increased level of alpha-2-macroglobulin, a collagenase inhibitor, in keloid lesions. Although the collagenase found in keloids appears to be similar to that of normal dermis, increased collagenase inhibitors may contribute to a lack of collagen degradation and, therefore, increased collagen deposition with abnormal scars.

The question of collagen type abnormalities in abnormal scars is raised frequently. After injury to normal skin, the ratio of Type III to Type I collagen increases and then subsides to a normal value of about 17 to 20% of total collagen as wound healing progresses. It is known that Type III collagen is increased in granulation tissue and in hypertrophic scars, but Type III collagen appears to occur in a normal amount in keloids. It has been reported that keloid fibroblasts overproduce Type I collagen, while Type III collagen expression remains unchanged. This finding also suggests that keloids are dissimilar to early wounds. This is surprising because other parameters such as elevated water content, increased soluble collagen, and increased histamine indicate that mature keloids resemble early wounds. It is possible that abnormal collagen types have not been found because of limitations of typing methodology. More sophisticated typing methods may identify abnormal ratios and types of collagen in abnormal scars.

There has never been a clear histologic difference between keloids and hypertrophic scars. Over two decades ago, one study differentiated keloids from hypertrophic scars on the basis that keloids appear to contain bundles of collagen with focal proliferation or nodules and increased quantities of mucopolysaccharides. Another more recent study reviewed the literature on histology of abnormal scars and reported that collagen in both keloids and hypertrophic scars is organized into discrete nodules, frequently (but not always) obliterating the rete pegs in the papillary dermis of the lesions. Whereas the collagen in normal dermis is arranged in discrete fascicles, separated by considerable interstitial space, the collagen nodules in keloids and in hypertrophic scars appear avascular and unidirectional, and are aligned in a "highly stressed" configuration. The origin and significance of characteristic collagen nodules in abnormal scars are unknown at the present time. While myofibroblasts have been found in keloids and hypertrophic scars, their role in abnormal scar formation remains obscure. The relationship between the histology and the pathophysiology of these lesions remains an enigma.

3. Pharmacologic Control

Pharmacologic treatment of lesions characterized by excessive collagen production has been historically directed toward either decreasing protein production (specifically collagen production) or enhancing collagen turnover by rendering the collagen molecule more soluble or more susceptible to enzymatic degradation. Steroids affect the former, and lathyrogens such as beta-aminoproprionitrile (BAPN) and penicillamine-D are agents used to accomplish the latter (Cohen et al, *Plastic Surgery, Vol. 1, General Principles*, pp. 732–747 (1990)).

Steroids have been shown to decrease the size of keloids in a number of clinical studies and decrease collagen synthesis in vitro studies, specifically performed on keloid and normal dermal fibroblasts. Surprisingly, collagen production as measured by propyl hydroxylase was not decreased in lesions previously treated with triamcinolone. Nevertheless, triamcinolone acetonide is the steroid of choice for intralesional treatment of keloids. Moderately insoluble intralesional triamcinolone acetonide has been claimed to be effective in reducing the size of the keloids and hypertrophic scars. It has also been suggested that keloid resorption after steroid treatment may, in part, be due to steroid enhancement of collagenase activity. There is data to suggest that corticosteroids not only inhibit protein synthesis, but also enhance collagenase activity.

4. Mechanical Control

Mechanical pressure has been reported to inhibit hypertrophic scar formation. It has also been hypothesized that mechanical pressure alters the glycosaminoglycan (GAG) content and the blood vessel permeability of healing wounds and thus subsequently curtails scar formation by altering normal collagen-GAG interaction during wound healing. Others have suggested that mechanical pressure increases tissue collagenase activity, which in turn prevents excessive collagen deposition, although this hypothesis has also not been substantiated. Nevertheless, pressure therapy is used widely to control abnormal scar formation after burn injury, for example, even though the mechanisms by which mechanical pressure works are unknown.

The procedure involves prolonged application of pressure wraps (four to 12 months for burn scars). In the case of keloids, a pressure earring may be applied to prevent their recurrence. Problems have been encountered, however, in that when the pressure is released for any length of time, hypertrophic scarring may occur. For example, one study attempted to treat sternal keloids by tissue expansion followed by tension-free wound closure. The data clearly demonstrated that keloids still recur in the presence of tension-free closure after skin expansion.

5. Radiation Control

The use of ionizing radiation as a means of treating keloids was first attempted in the early 1900's and thereafter with questionable success. Radiation non-selectively destroys collagen-producing fibroblasts in lesions as well as in surrounding connective tissue and cells—a significant drawback to its use. Even when combined with surgery and chemotherapy, radiation does not appear to provide an effective, preventive modality for abnormal scar or keloid formation. Although there are no known reports of radiation-induced carcinoma following treatment of abnormal scars with radiation, caution is always recommended because of this possibility.

6. Surgical Control

Manipulation of the type of suture material and experiments with different suture techniques have been proposed as methods of obviating possible abnormal scar formation. There are no data to suggest that the type of suture material or surgical closure technique is in any way involved in the etiology of abnormal scar (Cohen et al, *Plastic Surgery, Vol. 1, General Principles*, pp. 732–747 (1990)). However, tension and lines of relaxed skin tension may be related to hypertrophic scar formation. Wound closure parallel to the lines of relaxed skin tension usually produces fine-line scars, whereas wound closure perpendicular to the lines of relaxed skin tension tend to form hypertrophic scars.

VIII. Post Operative Intraperitoneal Adhesions

In addition to wound healing, scarring presents a problem in the area of postoperative intraperitoneal adhesions. For example, one of the major problems of intraabdominal surgery is the avoidance of postoperative adhesions. Bowel obstruction (Ellis, *Surg. Gynec. Obstet.*, 133: 417–431 (9171)) may ensue and, if female reproductive organs are involved, tubal infertility can result. In the field of reconstructive tubal surgery, postoperative adhesions are responsible for failure in 40% of the cases (Gordji, *Acta. Euro. Fertil.*, 6: 279–285 (1975)).

The extent of postoperative adhesion formation is the most important determinant of the outcome of infertility operations, and it is largely responsible for most of the observed failures with these procedures (Ellis, *Surg. Gynec. Obstet.*, 133: 417–431 (1971); Bronson et al, *Fertil. Steril.*, 18: 613 (1977)). An inverse relation-ship between the grade of adhesions and pregnancy rate, regardless of tubal condition, has been reported (Caspi et al, *Fertil. Steril.*, 31: 296 (1979)). Infections, foreign body reactions, and surgical trauma are the principal causes of intraperitoneal adhesions, and, to improve the results of infertility operations, great efforts have been directed at prevention of adhesions by the use of: 1) fibrin sealant; 2) amniotic fluid; 3) medical adjuvants; 4) less reactive sutures; and 5) microsurgical techniques.

1. Fibrin Sealant

For several years highly concentrated human fibrin sealant has been recommended for bowl anastomoses, liver repair, and spleen surgery (Yaita et al, *Japanese J. Surg.*, 5: 56–63 (1975) and Orda et al, *J. Surg. Res.* 17: 365–374 (1974)), mainly due to its reliable hemostatic effect. The intra-abdominal use of fibrin sealant is still a matter of debate. Fibrin sealant is a method of sealing peritoneal surfaces with physiological agents. The sealant gives a smooth surface and prevents exudates and bleeding. On the other hand, the sealant acts as a substrate for fibroblast proliferation (Staindl et al, *Arch. Otorhinolaryngol.*, 233: 105–166 (1981) and Hedelin et al, *Scand. J. Plast. Reconstr. Surg.*, 17: 179–181 (1983)) and thus may promote adhesions. One study (Lindenberg et al, *Ann. Chir. Gynaecol.*, 73: 11–13 (1984)) showed a protective effect when fibrin sealant was used to cover sutured parietal peritoneum in rats. In a second study on rats (Lindenberg et al, *Acta Chir. Scand.*, 151: 525–527 (1985)), it was demonstrated that adhesion formation was inversely correlated with the thickness and lifetime of the fibrin clot. However, even with a thin layer of fibrin, adhesion formation was significantly greater than in an untreated control group. Furthermore, fibrin sealant has been successfully used in humans (Baumann et al *Geburtsh Frauenheilkd*, 46: 234–236 (1986)) and in animals (Gauwerky et al, *Human Reprod.*, 3: 327–330 (1988)) for tubal surgery, with no increase in adhesion formation observed. Since the fibrin clot is an optimal substrate for the ingrowth of fibroblasts and consequent collagen synthesis and fibrosis, adhesion promoting qualities may result.

In tubal surgery, prevention of adhesions is mandatory. Only a few of the various methods for preventing adhesions have had satisfactory results (Gauwerky et al, *Vorbegung und Behandlung Fertilirtat*, 2: 125–134 (1986)), and this includes using anti-inflammatory drugs and barrier methods of isolating the injured area from adjacent tissues (Gauwerky et al, *Arch. Gynecol. Obstet.*, 247: 161–166 (1990)). Peritoneal grafts to cover deperitonealized surfaces have always been advocated for adhesion prophylaxis, although their use does not seem to be very rewarding (Soules et al, *Am. J. Obstet. Gynecol.*, 143: 829–834 (1982)). Benefit has been described for the use of a free peritoneal graft in bowel anastomoses (Yaita et al, *Japanese J. Surg.*, 5: 56–63 (1975)) and the repair of bile duct defects. Grafts, however, have a tendency to become necrotic, thereby inducing an increase in inflammation reaction and scar tissue formation, which can reinforce an anastomoses and interfere with the adhesion-free healing of deperitonealized surfaces. In one study (Gauwerky et al, *Arch. Gynecol. Obstet.*, 247: 161–166 (1990)), a peritoneal defect by ischemia was created and then covered by a tension-free graft kept in place with fibrin glue. The results of that study suggest that covering ischemic lesions with peritoneal grafts is ineffective in preventing adhesions. Whether this would hold true for non-hypoxic defects or trauma remains unclear. Such defects may heal without adhesion formation of their own (Ellis, *Surg. Gynec. Obstet.*, 133: 417–431 (1971) and Connolly et al, Int. Abstr. Surg., 110: 417–431 (1960)).

2. Amniotic Fluid

The relatively paucity of intraperitoneal adhesions following cesarean sections is an accepted observation among obstetricians. It was suggested (Johnson, *Surg. Gyn. Obstet.*, 45: 612 (1928a) and Johnson, *N. Engl. J. Med.*, 199: 661 (1928b)) over fifty years ago that possibly amniotic fluid can inhibit adhesion formation. Examinations have been made of postoperative course after leaving amniotic fluid intraperitoneally at the end of the surgery. These examinations noted a diminished extent of adhesions and related this observation to the presence of amniotic fluid and thus suggested the application of this fluid at the end of abdominal surgeries of all kinds in order to suppress adhesion formation. Subsequently, bovine amniotic fluid was processed into a medication called "Amfetin" and was used for more than a decade (1930–1945). However, other studies trying to reproduce the findings did not achieve uniform results. Some supported the findings (Warren, *Arch. Pathol.*, 6: 860 (1928); Kimpton, *N. Engl. J. Med.*, 207: 465 (1932); and Merkle, *Am. J. Surg.*, 65: 210 (1944)), others showed a partial effect (Gepfert, *Am. J. Surg.*, 32: 40 (1936); Trusler, *Arch. Surg.*, 22: 283 (1931)), and still others, none at all (Lacey, *Ann. Surg.*, 101: 529 (1935)). In the mid 1940's the subject was abandoned, and disappeared from the medical literature. However, the observation that there are fewer intraperitoneal adhesions following cesarean sections than following other pelvic operations is still valid in daily practice (Golan et al, *Int. J. Fert.*, 36: 317–320 (1991)). The major explanation of the phenomenon may lie in the major hormonal and immunological changes in pregnancy, the changes in the anatomical relationship between the very large uterus and the rest of the abdominal organs, or the effect of the intraperitoneal spillage of the amniotic fluid itself during the operation.

The effects of amniotic fluid on serosal surfaces, and mainly the peritoneum, was initially studied in the 1930's. Those studies (Johnson, *Surg. Gyn. Obstet.*, 45: 612 (1928a); Johnson, *N. Engl. J. Med.*, 199: 661 (1928b); and Warren, *Arch. Pathol*, 6: 860 (1928)) reported that the peritoneal inflammatory response (local leucocytosis and fibrin deposition) is faster and the oozing time of the inflammatory exudate shorter in the presence of amniotic fluid. These findings were supported by others (Trusler, *Arch. Surg.*, 22: 283 (1931) and Swolin, *Acta Obstet. Gynecol. Scand.*, 45: 473 (1966)). One of those early studies (Johnson, *N. Engl. J. Med.*, 199: 661 (1928b) proposed a beneficial effect of intraperitoneal application of amniotic fluid in 60–70% of the treated patients, inhibiting adhesion formation by one of the following mechanisms: (a) shortening the exudate oozing time, thus decreasing the deposition of blood and fibrin; (b) acting as a lubricating medium separating injured surfaces because of its slow absorption from the peritoneal cavity; or (c) a faster peritoneal healing related to "growth factors" that may exist in the amniotic fluid. Later studies on rats (Lacey, *Ann. Surg.*, 101: 529 (1935)) and on dogs (Gepfert, *Am. J. Surg.*, 32: 40 (1936); and Trusler, *Arch. Surg.*, 22: 283 (1931)) did not demonstrate a significant difference in the amount of adhesions between animals treated with amniotic fluid and controls. However, there was the impression that the adhesions were lighter and easier to separate.

During more than a decade, amniotic fluid was used clinically as a medication for adhesion prophylaxis. An early study (Kimpton, *N. Engl. J. Med.*, 207"465 (1932)) reported a faster postoperative recovery in about 400 major operations using amniotic fluid. A study a few years later (Gepfert, *Am. J. Surg.*, 32: 40 (1936)) compared 50 women treated with amniotic fluid to a control group and found an enhanced postoperative recovery. Subsequent similar studies (Merkle, *Am. J. Surg.*, 65: 210 (1944) and Rigdon et al, *Am. J. Surg.*, 53: 481 (1941)) reported similar observations. One study conducted during the above time period (Lacey, *Ann. Surg.*, 101: 529 (1935)), however, recording postoperative return of peristalsis, degree of abdominal pain, dilation of the stomach, nausea, vomiting, and leucocytosis, did not notice any improvement of postoperative recovery in patients treated with amniotic fluid.

Results from a recently completed study (Golan et al, *Int. J. Fert.*, 36: 317–320 (1991)) agree with (Lacey, *Ann. Surg.*, 90: 281 (1930)) experimental observations made over fifty years ago. Comparing amniotic fluid to saline controls, no inhibitory effect of the amniotic fluid was demonstrated. The effect of amniotic fluid and the control saline solutions on fibroblast proliferation was examined in vitro using fibroblastic cell cultures. No direct effect on fibroblast proliferation was found. The conclusion of the aforementioned recent study (Golan et al, *Int. J. Fert.*, 36: 317–320 (1991)) was that it was not the direct effect of the spillage of amniotic fluid that inhibits adhesion formation after the performance of cesarean sections.

3. Medical adjuvants

Medical adjuvants have been used by infertility surgeons to decrease the body's inflammatory responses to tissue injury (Pfeffer et al, *Fertil. Steril.* (1980)), however, the benefits derived from medical adjuvant therapy remain controversial. The most commonly used pharmacologic agents aimed at preventing postoperative adhesion formation include corticosteroids, antibiotics, and intraperitoneal administration of high-molecular weight dextran (Pfeffer et al, *Fertil. Steril.* (1980)). Recently, non-steroidal, anti-inflammatory agents have been tested in animal studies, and both ibuprofen and oxyphenbutazone have been reported to inhibit postoperative adhesion formation in rabbits (Siegler et al, *Fertil. Steril.*, 34: 46 (1980)) and rats (Larsson et al, *Fetil. Steril.*, 18: 807 (1977)).

Another study (Luciano et al, *Amer. J. Obstet. Gynecol.*, 146: 88–92 (1982)) examined the relative efficacy of dexamethasone, ibuprofen, and 32% dextran 70 (Hyskon) in the prevention of both postoperative adhesion formation and the inflammatory tissue reaction in the reproductive tissues of the rat. Of the three major groups examined, the dexamethasone-treated animals formed the least postoperative adhesions. Other studies have demonstrated similar findings (Siegler et al, *Fertil. Steril.*, 34: 46 (1980); Scheinberg et al, *Arch. Surf.*, 63: 413 (1951)). In contrast some studies (Gomel, *J. Reprod. Med.*, 18: 181 (1977); (Pfeffer et al, *Fertil. Steril.*, in press (1982); and (Seitz et al, *Fertil. Steril.*, 24: 935 (1973)), showed no beneficial effects of corticosteroids in the prevention of postoperative adhesion formation in rats, rabbits and monkeys, respectively. The only well-controlled prospective clinical study (Swolin, *Acta Obstet. Gynecol. Scand.*, 45: 473 (1966)) showed that intraperitoneal administration of hydrocortisone was associated with significantly fewer adhesion formations than the control group, as assessed by laparoscopy performed three months postoperatively.

In rabbits, one study (Siegler et al, *Fertil. Steril.*, 34: 46 (1980)) found that intravenous administration of ibuprofen significantly inhibited postoperative adhesion formation as effectively as dexamethasone. In rats, another study (Luciano et al, *Amer. J. Obstet. Gynecol.*, 146: 88–92 (1982)) found that, although fewer adhesions were formed in the ibuprofen-treated animals than in the control animals, the difference was not statistically significant. The discrepancy may be due to species differences or to use of intraperitoneal administration of ibuprofen, which has been reported to be less effective than the intravenous route in preventing postoperative adhesion formation.

Several studies have reported the efficacy of 32% dextran 70 (Hyskon) in preventing postoperative adhesions ((Pfeffer, *Fertil. Steril.* (1980)), but the mechanism of action remains unknown. Some investigators have theorized that dextrans are antithrombogenic and capable of preventing clot formation. Others (Ellis, *Surg. Gynec. Obstet.*, 133: 417–431 (1971)) have proposed that dextrans act as osmotic gradients to increase the constituents of the intraperitoneal fluid, thereby preventing tissue opposition during the crucial stages of repair. One group of studies (Luciano et al, *Amer. J. Obstet. Gynecol.*, 146: 88–92 (1982)) supports the previous observations that dextrans are of significant benefit in the prevention of postoperative adhesions. However, the histopathologic evaluation noted similar granulomatous inflammatory reaction in Hyskon-treated and non-treated animals, suggesting that although Hyskon is effective in preventing scar formation between separate surfaces, it does not have significant inhibitory effects on the local inflammatory responses of tissues to injury or foreign body. These findings support the hypothesis that the mechanism of action of 32% dextran 70 involves producing an intraperitoneal floating bath that prevents tissue opposition and contact between raw surfaces during the crucial stages of surface re-epithelialization.

4. Less reactive sutures

Less reactive sutures have been suggested as a method to decrease foreign body reaction (Riddick et al, *Fertil. Steril*, 28: 1220 (1977)). Studies comparing Dexon-S and coated Vicryl sutures (Luciano et al, *Amer. J. Obstet. Gynecol.*, 146: 88–92 (1982)) showed them to be very similar to physical characteristics, overall handling, and their elicitation of the foreign body tissue reaction. Since the densest adhesions and the most severe inflammatory reaction occurred around the surgical knots, the use of square knots with only two throws and, where possible the burying of the knots under the serosa or use of a running suture to approximate the superficial layers was recommended.

5. Microsurgical techniques

Microsurgical techniques to minimize tissue trauma in tubal reconstruction have been widely recognized (Gomel, *J. Reprod. Med.*, 18: 181 (1977)). Microsurgery has come to connote not only the use of magnification, but the whole concept of fine surgery which embodies the discipline of gentle handling and the constant irrigation of tissues, meticulous hemostasis, the use of microsurgical instruments, the use of fine sutures, and precise tissue approximation (Gomel, *J. Reprod. Med.*, 18: 181 (1977); and Siegler et al, *Fertil. Steril.*, 32: 377 (1979)). One study (Luciano et al, *Amer. J. Obstet. Gynecol.*, 146: 88–92 (1982)) demonstrated, however, that when these principals were strictly adhered to with excellent tissue approximation, and patency of the areas of anastomosis being obtained in animals, postoperative adhesion formation was not prevented in the absence of medical adjuvants.

IX. Repair and Grafting of Skeletal Muscle

It is generally believed that the source of the regenerative process in skeletal muscle is the activation of the dormant stem cell known as the myosatellite cell identified by Mauro in 1961 (Snow, *Cell. Tiss. Res.*, 186: 535 (1978)). These cells are located beneath the basement membrane of the muscle fiber, and under conventional light microscopy appear identical to muscle cell nuclei. They can be identified by electron microscopy and are observed through the muscle, making up 2 to 35% of the total number of nuclei, depending on the age of the animal. The number of myosatellite cells has been shown to increase after denervation.

It appears that the myosatellite cell is capable of surviving periods of ischemia that result in necrosis of mature muscle fibers and initiating the regeneration process when the neovascularization wave moves through the graft. The potential for longer survival by the myosatellite cell may be attributed to a low metabolic rate due to a very small amount of cytoplasm, thus allowing these cells to survive by plasmic imbibition (Snow, *Anat. Rec.*, 188: 181 (1977)).

In reconstructive surgery it is routine to transfer all varieties of tissue from one anatomic location to another with a high expectation of success. Grafts of skin, bone, tendon, cartilage, and nerve are common, the notable exception has been skeletal muscle. Until recently it was generally agreed that this metabolically demanding tissue could not be grafted. However, the successful transfer of contractile muscle into a functionless area must be considered a goal of the highest priority in reconstructive surgery (Miller, *Plastic Surgery*, Vol. 1. General Principles, pp. 546–558 (1990)).

In order to graft other tissue such as skin or cartilage, it is only necessary to acquire a new blood supply to be successful. Muscle grafting is much more complex, involving other variables such as the balance of physiologic tension between points of origin and insertion, innervation, and blood supply. Altering any of these factors even in situ results in compromise of muscle function or death.

It is known that following motor nerve severance muscle atrophies and is eventually replaced by fibrous tissue. Detailed investigations into the denervation process have ben summarized in studies. Denervated muscle or muscle graft can become innervated by one of three mechanisms: surgical neurohaphy; implantation of nerve directly into the muscle; and sprouting of nerves from adjacent normal muscle, i.e., muscular neurotization. In clinical situations in which a nerve is not available, the latter mechanism is predominant. The phenomenon of one muscle innervating another has been observed clinically. One study noted that following a pharyngeal flap there is often reanimation of surrounding soft palate musculature. In failed neurotization it is likely that fascia is a barrier to the reinnervation between muscles. Most reports of free muscle grafts in humans have occurred in reconstruction of facial and anal muscles, neither of which have fascial coverings.

Reinnervation is probably the single most important aspect of the repair process of muscle as well as the most time-consuming, even when surgical neurorhaphy is performed. One study has reported that after successful microneurovascular transfer no muscle contraction was identified for five months.

It is not known how long a muscle can exist before irreversible atrophy and fibrosis makes attempts to introduce neural innervation unsuccessful. It is likely that different muscles undergo atrophy at different rates. It has been observed that intrinsic muscles of the hand atrophy within months after denervation, yet successful reinnervation of facial muscles has been reported one year after facial nerve injury. There seems little question, however, that the longer the period of denervation, the more unsuccessful is the reinnervation process. Alterations in the normal physiologic length of muscle adversely influence function. It is well known from clinical experience that after an unrecognized tendon laceration, reduction of the resting length of the muscle results in atrophy, fibrosis, and loss of normal elasticity within a few weeks of injury. If insufficient resting tension exists, the muscle fibers decrease in cross sectional area and shorten in length, thus limiting motor function and strength. It is also true that increasing the length of a muscle and applying excessive stretch results in fibrosis and loss of contractile force.

It has been recognized that skeletal muscle has the potential for repair following injury or disease. Sporadic reports have suggested that muscle has the regenerative capability of healing after crush injury, small lacerations, and infection, such as typhus.

Although lacerations of muscle are common in clinical practice, little attention has been focused on the study of functional recovery. One study found that completely lacerated (transected) muscles recovered approximately 50 percent of their ability to produce tension and were able to contract (against a minimal weight) at a level 80% of normal. After partial lacerations of the muscle, 60% of the tension production and normal shortening were observed. The muscle laceration was noted to heal by scar formation, but it should be pointed out that the extremities of the animals used in this study were not immobilized following injury. The portion of the muscle distal to the transection showed microscopic evidence of denervation atrophy: small irregular-shaped muscle cells with central positioning of the nuclei, and an increased amount of fibrous tissue. The denervated segment did not stretch during contraction, probably because of the increased content of fibrous tissue.

The importance of innervation to the repair or regeneration process within the muscle is profound. Following injury, regenerative activity takes place but does not continue unless a nerve supply is present. For example, palmaris longus muscles have been grafted in the rhesus monkey with and without surgical repair of the median nerve. No vascular repair was performed. Muscle fibers regenerated in all grafts in which neural repair was done, but only in three of eight autografts without nerve repair.

A muscle graft is a muscle completely removed from its origin, insertion, and nerve and blood supply and replaced into the original bed (orthotopic) or another anatomic location (heterotopic). Some of the earliest and most extensive laboratory work on free muscle grafting was done in Russia. In 1960, reputedly the first successful muscle graft was performed, transferring the middle third of the gastrocnemius of the rat. Subsequently, the regenerative capacity of muscle was confirmed when "minced" (cut into 1 mm cubes) was found to reform the rat gastrocnemius muscle provided that the tendon of insertion and the nerve were left in place. It was believed that mincing stimulated myoblasts into "mitotic division". At that time the concept of preoperative denervation was also introduced, a maneuver thought to induce a "plastic state" of regenerative activity within the muscle: enlargement and division of nuclei, amitotic division of the nuclei, the growth of sarcoplasm masses and the formation of myofibrils. In 1971, the first report of successful free muscle grafts in humans occurred, principally in the surgical efforts to reanimate the face following seventh nerve palsy.

From animal and human studies, it appears that the size of the graft is a critical factor in determining whether or not complete regeneration will occur or whether a residual area of central necrosis will remain. Complete regeneration occurs throughout the entire muscle in the rat extensor digitorum longus (100 mg) and the rabbit flexor digitorum sublimis (1.5 gm). However, a persistent core of necrosis, which is eventually replaced by scar tissue, has been observed in the cat extensor digitorum (3.5 gm) and the monkey palmaris longus (4.5 gm). This difference suggests that a critical factor in regeneration is the radius of the graft. This may be due to the time necessary for centripetal vascular penetration to reach the center of the graft and provide nourishment to the residual myogenic cells. The regeneration cycle is complete within 60 days in the rat, 90 days in the rabbit, and 180 days in the cat.

X. Repair and Grafting of Peripheral Nerve

During Wallerian degeneration, pluripotential Schwann cells assume the dual role of degradation of the myelin and axonal debris, and they proliferate within the basal lamina of the remaining endoneurial connective tissue sheath (Satinsky et al, *Exp. Neurol.*, 9: 441 (1964)). As they proliferate they become densely packed in longitudinal rows histologically recognized as the bands of Bunger. They are ready to accept axon buds and remyelinate the advancing regenerating axons (Selzer, *The Physiology of Peripheral Nerve Disease*, pp. 358–431 (1980) and (Thomas et al, *Greenfield's Neuropathology*, (1984)). During Wallerian degeneration and proximal axonal regeneration, collagen fibrils are also deposited externally to the persisting basal lamina tubes—especially near the site of axonal severance. Deposition of collagen fibrils continues until regeneration is completed (Thomas, *J. Cell. Biol.*, 23: 375 (1964)) and (Thomas et al, *Greenfield's Neuropathology,* (1984)). The more time it takes for the distal nerve stump to become reinnervated, the more collagen is laid down, and consequently the thickened endoneurial tube decreases in internal diameter (Holmes et al, *J. Anat.*, 77: 63 (1944)). Not only does this thickening decrease the available potential area for axonal reentry, but the thickened tubes create a local constriction of the growing axon. This restricts the ultimate axonal diameter and leads to permanent reduction in axonal size and myelin thickness (Weiss et al, *Proc. Soc. Exp. Biol.,* 55: 77 (1944) and (Holmes et al, *J. Anat.,* 77: 63 (1944)). If a healthy vascular bed is not maintained or created, the neurosatellite cells and support structures of the regenerating nerve suffer an ischemic insult, and increased collagen deposition results. The character of the collagen deposition under conditions of ischemia is consistent with the type of collagen found in dense mineralized tissue scar. This type of collagen matrix presents a greater obstacle to axonal regeneration than that found in nonischemic nerve (Starkweather et al, *J. Hand Surg.,* 3: 163 (1978)).

Unfortunately, beginning between 28 and 35 days after a nerve lesion (during a period of active regeneration), there is a deposition of an additional layer of endoneurial collagen. This narrows the potential space available for axonal growth. Despite the peripheral migration of the Schwann cells to open the center of the endoneurial cylinder for axonal growth, the ultimate diameter of the regenerated axon is decreased (Thomas, *J. Cell, Biol.,* 23: 375 (1964)). The overall number of Schwann cells per unit length is increased, and after remyelination of the regenerated axon this is reflected in a decreased internodal length (Gragg et al, *J. Physiol. (Lond.),* 171: 164 (1964) and (Thomas et al, *Greenfield's Neuropathology, (*1984)).

Since the connective tissue elements of the distal nerve fiber are dependent on the presence of an intact axon to maintain anatomic, metabolic, and functional integrity, failure of regeneration of a nerve eventually leads to irreversible shrinkage of the distal endoneurial tube. Within two years, the cross sectional area of the empty endoneurial sheath will be only 1% of its original normal size. The blood supply of the distal nerve fiber also undergoes contraction and reexpands following regeneration of the nerve.

When a nerve injury results in disruption of the basal lamina (basement membrane), there is no longer the regenerative specificity that is possible with an intact endoneurial tube. The greater the disruption of the basal lamina, the lower the likelihood of an end organ specific regeneration (Terzis et al, *Plastic Surgery, Vol,* 1, *General Principles* pp. 630–697 (1990)). With transection of the nerve axons, the fascicular disruption that defines this injury allows greater stump retraction proximally and distally. However, the intact epineurium limits the extent and confines the interposed scar. Budding axons become entangled in the scar and few succeed in bridging the gap between the stumps. The few sprouts that find their way to the degenerating distal stump lengthen, mature, and remyelinate, but distal functional connectively is haphazard (Ducker et al, *J. Neurosurg.,* 30: 270 (1969); (Mira, *Int. J. Microsburg,* 3: 102 (1981b); and Cabaud et al, *J. Hand. Surg.,* 71: 159–171 (1982)). These lesions are clinically detected as neuroma-in-continuity masses of misdirected axons entangled within the scar confined by the epineurium. Some budding axons can follow perineurial and epineural blood vessels and "escape" the nerve trunk to become a lateral neuroma (Daniel et al, *Reconstructive Microsurgery,* (1977b)).

Loss of a portion of the nerve results in separation of the entire proximal and distal stumps. The normal regenerative pattern of the proximal stump proceeds, but growth cones and their accompanying Schwann cells grow into random scar tissue separating the ends. The more disoriented the substratum, the more the growth cone sprouts will branch. Miniature fascicles in random orientation, embedded in dense connective tissue scar, are the result-neuroma of amputation (Weiss et al, *Proc. Soc. Exp. Biol.,* 55: 77 (1944) and (Spencer, *Reconstructive Microsurgery,* pp. 342–349 (1977)). It is virtually impossible for this lesion to regenerate without some form of directional guidance to the distal stump.

When an axon is severed and unable to reestablish continuity with its distal counterpart, a neuroma forms. This process begins at the proximal stump by the sprouting of axons from the growth cones and the proliferation of Schwann cells after the neuron has recovered from the retrograde reaction (Wallerian degeneration). Fibroblastic proliferation, encouraged by blood clot, foreign body, or necrotic debris, occurs between the proximal and distal stumps and impedes the regenerating axons and Schwann cells. The regenerating fibers haphazardly grow and branch, and abundant, irregular ramifications of axons are created in their abortive attempt to reach their end organs (Williams et al, *Plast. Reconstr. Surg.,* 57: 562 (1976)).

The overall configuration of a neuroma depends largely on the characteristics of the local environment. Since fibers have no intrinsic tendency to branch, the more confused and dense the substratum, the more profuse is the branching. If the scar tissue at the proximal stump is diffuse and radiates into the surrounding tissues, the growing axons and proliferating Schwann cells follow. If the scar has tightly capped the stump, the entrapped fibers circle within, forming whorls, and in some instances the axons turn back on themselves and form irregular spirals within the substance of the proximal stump. The regenerating axons are not seen to stop short, but continue to proliferate without apparent direction, giving rise to the bulging clinically observed (Weiss et al, *Proc. Soc. Exp. Biol.,* 55: 77 (1944)).

In general, the natural wound healing mechanism of the body runs counter to what would be in the best interest of nerve healing and subsequent regeneration. Scar formation between the proximal and distal ends of a coapted nerve physically blocks the forward growth of the axons and causes the nerve growth cones to branch, divert, turn back, or terminate. Axons and Schwann cells have the tendency to align themselves along linear structures; therefore, the confusing substratum of an interposed scar creates a tangled mass of misdirected fibers, few of which reach the distal stump. Under satisfactory conditions following nerve transection, it has been estimated that only one-sixth or one-seventh of the sprouting axons in an adult reach the distal stump and go on to grow distally. A higher percentage of growth has been observed in young patients (Weiss et al, *Proc. Soc. Exp. Biol.,* 55: 77 (1944)). Therefore, scar development in the regenerating nerve's bed represents an obstacle to both longitudinal growth and growth in diameter during maturation.

From the above discussion, two things are clear. First, despite copious experimentation in connection with the healing of wounds, many questions remain unanswered. These unanswered questions demonstrate how much is yet unknown. Secondly, the scientific and medical community have approached the healing of wounds from the standpoint of encouraging scar formation (to initially close the wound) subject to such scar formation not thereafter turning abnormal.

Although scar formation can pose potential problems, thus far the benefits of scar formation associated with wound closure have outweighed the potential complications. Of course the optimal condition would be for wounds to heal without scar formation, thereby obviating concerns over potential complications.

It is thus apparent that a need exists for a composition and method of using same to inhibit scar formation. While the product and method of this invention is particularly suited for use with skin, it is contemplated that the invention would be useful with other tissue phenotypes, e.g. muscle, bone, etc.

SUMMARY OF THE INVENTION

There is disclosed a protein isolate comprising one or more water soluble proteins isolated from basement membranes, wherein the protein isolate selectively inhibits stem cell fibroblastic lineage commitment and differentiation in vitro and in vivo. Alternatively the protein isolate may comprise one or more water soluble proteins isolated from bone, wherein the protein isolate also selectively inhibits stem cell fibroblastic lineage commitment and differentiation in vitro and in vivo.

The protein isolate is preferably isolated from mammalian basement membranes or bone. The protein isolate preferably has its proteins extracted with a solution selected from the group consisting essentially of guanidine hydrochloride, urea, EDTA and salt solutions. The resultant inhibition of stem cell fibroblastic differentiation can occur in vivo with minimal proliferation of scar connective tissue cells. The resultant inhibition of stem cell fibroblastic lineage commitment and differentiation into scar-associated connective tissue structures can occur in vivo and in vitro.

The protein isolate can be utilized in combination with a delivery vehicle providing controlled release of the protein isolate at a site where scar tissue inhibition is desired. The delivery vehicle is preferably a natural or synthetic polymeric controlled release matrix.

The drug delivery device preferably has a genetically-engineered SIF gene inserted into a mesenchymal stem cell and injected into a mammal, animal or human as a drug delivery device. The polymer of the polymeric controlled release matrix is selected from the group consisting essentially of biocompatible, bioerodible and non-erodible polymers. The bioerodible polymer is selected from the group consisting essentially of surface eroding polymers and bulk eroding polymers. The delivery vehicle may also be a transdermal drug delivery device.

There is also disclosed a method for isolating a protein inhibiting fibroblastic lineage commitment and differentiation of stem cells into a scar phenotype from basement membranes and extracting the water soluble proteins to form a scar inhibitory protein isolate. This method further comprises the step of purifying the isolate by size exclusion chromatography isolating proteins greater than 50,000 daltons and by ion exchange chromatography. This method also further comprises the step of purifying the isolate by gel electrophoresis.

There is also disclosed a method for isolating a protein inhibiting fibroblastic lineage commitment and differentiation of stem cells into a scar phenotype from bone and extracting the water soluble proteins to form a scar inhibitory protein isolate. The method further comprises the step of purifying the isolate by size exclusion chromatography isolating proteins greater than 50,000 daltons and by ion exchange chromatography. The method further comprises the step of purifying the isolate by gel electrophoresis.

There is also disclosed a method of inhibiting scar tissue formation in a patient comprising administering a therapeutically effective amount of a water soluble protein isolate extracted from basement membranes to stem cells to prevent fibroblastic lineage commitment and differentiation. The protein isolate prevents stem cell differentiation and is administered to a wound to prevent scar tissue formation and allow normal regeneration to occur. The protein isolate is administered to said patient in a therapeutically effective amount of between approximately 1 pg and 10 mg/Kg body wt. Preferably the protein isolate is incorporated into a delivery vehicle for providing controlled release of the protein isolate at a site where inhibition of scar tissue formation is desired. Preferably the delivery vehicle is a natural or synthetic polymeric controlled release matrix comprising at least one polymer and with the matrix implanted in said patient for delivery of the protein isolate to the site.

The protein isolate is preferably administered to a patient having quantities of endogenous morphogens sufficient for the regeneration of skeletal muscle, smooth muscle, cardiac muscle, bone, cartilage, fat, peripheral nerves, ganglia, structural connective tissue, tendon, tendon sheaths, ligament, heart, liver, pancreas, gall bladder, stomach, intestine, kidney, adrenal gland, urinary bladder, brain, spinal cord, ovary, uterus, fallopian tubes, testes, vas deferens, prostate gland, seminal vesicles, lung, thymus, lymph nodes, blood vessels, skin, sensory end organs, nails, sebaceous glands, sweat glands and hair.

The protein isolate is preferably administered in combination with one or more compounds selected from the group consisting essentially of inducers of cell proliferation, inducers of cell differentiation, antibiotics, and anti-inflammatory agents. The protein isolate has a gene encoding the scar inhibitory protein, said gene being isolated and inserted directly into cells so that their synthesized product can be used in an endocrine, paracrine, or autocrine fashion to inhibit mesenchymal stem cell differentiation into scar fibroblasts and subsequent scar tissue formation.

The patient to whom the protein isolate is administered preferably has a disorder selected from the group consisting essentially of normal scars, hypertrophic scars, keloids, fibrous adhesions, full and partial thickness burns, fibrosis, cirrhosis, cysts, scleroderma, appendicular adhesions, intracranial adhesions, intrathoracic adhesions, intraabdominal adhesions, intraperitoneal adhesions, muscle transections, muscle tears, muscle grafting, muscle tethering, muscle atrophy, muscle damage by ischemia, muscle damage by infarction, decubitus ulcers, pressure ulcers, tissue damage due to vascular insufficiency, tendon transection, tendon tears, tendon grafting, tendon tethering, ligament transection, ligament tears, ligament grafting, ligament tethering, nerve transection, nerve tears, nerve grafting, nerve tethering, laminectomies, spinal cord transection, nerve block injuries, carpal tunnel syndrome, tendon synovitus, tendon sheath tethering, fibromas, neurofibromas, fibroblastomas, neurofibroblastomas, carcinomas, sarcomas, lipomas, tumors, muscular dystrophy, rheumatoid arthritis, systemic lupus erythematosus, myastenia gravis, multiple sclerosis, aneurysms, hemorrhage, and improperly aligned orthopedic prostheses.

There is also disclosed a method of inhibiting scar tissue formation in a patient comprising administering a therapeutically effective amount of a water soluble protein isolate extracted from bone to stem cells to prevent lineage commitment and differentiation. The protein isolate prevents stem cell differentiation and is administered to a wound to prevent scar tissue formation and allow normal regeneration to occur. The protein isolate is administered to said patient in a therapeutically effective amount of between approximately 1 pg and 10 mg/Kg body wt. Preferably the protein isolate is incorporated into a delivery vehicle for providing controlled release of the protein isolate at a site where inhibition of scar tissue formation is desired. Preferably the delivery vehicle is a natural or synthetic polymeric controlled release matrix comprising at least one polymer and with the matrix implanted in said patient for delivery of the protein isolate to the site.

The protein isolate is preferably administered to a patient having quantities of endogenous morphogens sufficient for the regeneration of skeletal muscle, smooth muscle, cardiac muscle, bone, cartilage, fat, peripheral nerves, ganglia, structural connective tissue, tendon, tendon sheaths, ligament, heart, liver, pancreas, gall bladder, stomach, intestine, kidney, adrenal gland, urinary bladder, brain, spinal cord, ovary, uterus, fallopian tubes, testes, vas deferens, prostate gland, seminal vesicles, lung, thymus, lymph nodes, blood vessels, skin, sensory end organs, nails, sebaceous glands, sweat glands and hair.

The protein isolate is preferably administered in combination with one or more compounds selected from the group consisting essentially of inducers of cell proliferation, inducers of cell differentiation, antibiotics, and anti-inflammatory agents. The protein isolate has a gene encoding the scar inhibitory protein, said gene being isolated and inserted directly into cells so that their synthesized product can be used in an endocrine, paracrine, or autocrine fashion to inhibit mesenchymal stem cell differentiation into scar fibroblasts and subsequent scar tissue formation.

The patient to whom the protein isolate is administered preferably has a disorder selected from the group consisting essentially of normal scars, hypertrophic scars, keloids, fibrous adhesions, full and partial thickness burns, fibrosis, cirrhosis, cysts, scleroderma, appendicular adhesions, intracranial adhesions, intrathoracic adhesions, intraabdominal adhesions, intraperitoneal adhesions, muscle transections, muscle tears, muscle grafting, muscle tethering, muscle atrophy, muscle damage by ischemia, muscle damage by infraction, decubitus ulcers, pressure ulcers, tissue damage due to vascular insufficiency, tendon transection, tendon tears, tendon grafting, tendon tethering, ligament transection, ligament tears, ligament grafting, ligament tethering, nerve transection, nerve tears, nerve grafting, nerve tethering, laminectomies, spinal cord transection, nerve block injuries, carpal tunnel syndrome, tendon synovitus, tendon sheath tethering, fibromas, neurofibromas, fibroblastomas, neurofibroblastomas, carcinomas, sarcomas, lipomas, tumors, muscular dystrophy, rheumatoid arthritis, systemic lupus erythematosus, myastenia gravis, multiple sclerosis, aneurysms, hemorrhage, and improperly aligned orthopedic prostheses.

One aspect of the present invention provides a protein isolate for inhibiting scar tissue formation.

Another aspect of the present invention provides for improved healing in patients suffering from a wide range of disorders.

Another aspect of the present invention provides for a method for inhibiting scar tissue formation.

Another aspect of the present invention provides for a method for improving healing in patients suffering from a wide range of disorders.

Other aspects and advantages of the instant invention will be apparent from the following description, examples, and the appended claims.

DETAILED DESCRIPTION OF THE INVENTION

Figure 1:
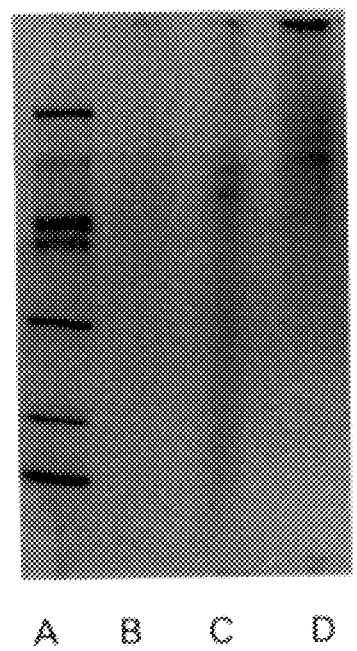
FIG. 1 discloses the results of a sodium dodecyl sulfate-polyacrylamide gel electrophoresis of the scar inhibitory factor protein isolate of this invention run under non-reduced conditions.

Specifically, the present invention is concerned with a protein isolate for inhibiting scar tissue formation. The present invention is also concerned with providing a substance for improved healing of patients suffering from a wide range of disorders. The present invention is also concerned with a method for inhibiting scar tissue formation. Finally, the present invention is concerned with a method for improving healing in patients suffering from a wide range of disorders.

The approach of the medical community when it comes to scar tissue formation is to encourage the formation of scar tissue, despite the potential complications associated with its formation, and then to hopefully avoid the potential complications. This approach is taken because of the problems that can occur related to an open wound. This invention represents a total departure from the prior approach by discouraging the formation of scar tissue and by encouraging the healing of wounds absent the formation of scar tissue.

It is thus apparent that a need exists for a composition to limit fibroblastic lineage commitment and differentiation of stem cells in vivo and in vitro thereby inhibiting scar formation. While the product of this invention is particularly suited for use with skin, it is contemplated that the invention would be useful with other tissue phenotypes, e.g., muscle, bone, etc.

Based on review of the prior art studies and investigation, it is believed that the Scar Inhibitory Factor (SIF) of this invention is a binding protein isolate with the potential to either bind directly to a "scar" morphogenetic protein; acting as a competitive inhibitor, to bind to a cell; surface receptor for the scar morphogenetic protein; or to bind to a closely associated cell surface receptor that can block the scar morphogenetic protein receptor. Scar morphogenetic protein is what induces the differentiation of resident mesenchymal stem cells into "scar" fibroblasts. These scar fibroblasts are subsequently involved in the deposition of extracellular matrix material forming normal scars, hypertrophic scars, keloids, and/or fibrous adhesions.

SIF is comprised of one or more heretofore unidentified non-collagenous proteins comprising basement membranes. Intact basement membranes, located between epithelia/endothelia/parenchyma and the underlying connective tissues, provide a supportive structure and effectively form a mechanical barrier to inhibit fibroblast infiltration and scar formation. SIF assists the mechanical action of the basement membrane by forming a chemical barrier, radiating from the basement membrane, to competitively inhibit the action of scar morphogenetic protein. SIF thereby assists inhibiting scar fibroblast formation and their subsequent infiltration through the basement membrane, thus preventing scar formation.

As discussed below in both in vitro and in vivo model systems, SIF is neither a cytotoxic agent of stem cells, a growth inhibitor of stem cells, nor does it affect the differentiation potential of the mesenchymal stem cells into other tissue phenotypes, i.e., muscle, cartilage, bone, fact, and/or structural fibroblasts. SIF's only discovered activity to date appears to be the inhibition of differentiation of mesenchymal stem cells into scar fibroblasts, thereby allowing normal differentiation to occur.

The scar inhibitory factor protein isolate of this invention can be obtained from the basement membranes (i.e., the extracellular matrix materials between epithelia/endothelia/parenchyma and the underlying supporting connective tissue/stroma) of skin, kidneys, placenta, eyes, skeletal muscle, peripheral nerves, the brain, the liver, the uterus, blood vessels, the gastro-intestinal system, the urogenital system, the reproductive system, or cortical bone for example. An enriched source of this material occurs in the Engelbreth-Holm Swarm (EHS) basement membrane sarcoma.

The protein isolate of this invention is preferably extracted with a solution such as guanidine hydrochloride (Gdn-HCl), Tris-hydrochloride (Tris-HCl), or sodium chloride (NaCl) in a concentration of at least 0.5M as follows. The extract is purified with dialysis or ultracentrifugation, passed over a DEAE-Sepharose column in urea where it is found in the unbound fraction, subjected to chromatography over a molecular seive column such as a Sepharose™ CL-6B column or Sephadex™ G-25 where it is in those fractions with proteins of molecular weights greater than 50,000, subjected to salt gradient chromatography over a cation-exchange column SP-Sephadex™ at pH 6.0, subjected to heparin-Sepharose affinity chromatography, followed by reverse phase HPLC or electroelution from an SDS-PAGE or native PAGE.

EXAMPLE 1
Isolation from EHS Basement Membrane Sarcoma

Propagation of the EHS basement membrane sarcoma was performed by serial passage in C57/BL or Swiss-Webster™ mice using subcutaneous implantation of minced tumor tissue. The tumor tissue was harvested and homogenized in 3.4M NaCl containing 0.05M Tris-HCl, 0.002M N-ethylmaleimide (NEM), and 8.0 mM ethylenediaminetetraacetic acid (EDTA), pH 7.4, at 4° C. The tumor tissue was then extracted at 4° C. with 4.0M guanidine hydrochloride, 0.05M Tris-hydrochloride, pH 7.4, containing 2.0 mM dithiothreitol, 0.002M N-ethylmaleimide (protease inhibitor) and 8.0 mM ethylenediaminetetraacetic acid (protease inhibitor). The extract preferably is further purified by either dialysis to water or ultrafiltration with an Amicon™ YM10 membrane, extraction at room temperature with a solution of Eagle's™ minimal essential medium containing Earle's salts at a pH of 7.4 with a solution to extract ration of 20:1, chromatography over a Sepharose G-25 column where it is found in the void volume, followed by electroelution from a native gel after polyacrylamide gel electrophoresis. This results in obtaining SIF protein isolate.

EXAMPLE 2
Isolation from Bovine Cortical Bone

Mid-shaft femoral cortices of one year old steers were cleaned, ground into pieces less than 1 cm$^3$ in a hammer mill, defatted in a chloroform, methanol solution (1:1) for 48 hours, rinsed with methanol, and air dried overnight to a constant weight. The bone chips were then extracted with a 4M guanidine hydrochloride (GuHCl) solution, pH 7.0, containing protease inhibitors (382 g GuHCl, 6.05 g Tris Base, 0.625 g N-ethylmaleimide, 1 ml of 0.1 mM phenylmethylsulfonyl fluoride in 100% ethanol, and 0.33 g sodium azide with double distilled water to 1.0 liter). Four ml of solution was added for each gram of bone. The resultant solution was stirred for 96 hours, followed by three extensive washes with double distilled water.

The bone chips were decalcified at 4° C. by either a 0.6N HCl solution or a 0.5M ethylenediaminetetraacetate (EDTA) solution. The decalcifying solution contains protease inhibitors in the guanidine solution, pH 7.0. The bone chips were re-extracted for five days at 4° C. in a solution of a 4M GuHCl buffered 50 mM Tris, pH 6.8, containing protease inhibitors described above. The resulting 4M GuHCl extract was dialyzed at 4° C. sequentially against solutions of decreasing strength: 0.5M GuHCl, 50 mM Tris, and finally distilled water.

The EDTA extracts were pooled and concentrated into three aliquots of 300 ml each by Amicon™ ultrafiltration with a YM10 membrane. Each 300 ml EDTA aliquot was washed with five liters of double distilled water. Precipitates formed at each step were removed by centrifugation until only those proteins soluble in cold distilled water remain. This portion of the extract was lyophilized and constituted a water soluble fibroblast inhibitory protein isolate.

The lyophilized protein isolate was dissolved in 6M urea, 50 mM Tris, 0.01% Triton™ X-100, pH 6.0, and the protease inhibitors described above. It was then passed over a DEAE-Sepharose™ column where it is found in the unbound fraction. The unbound fraction was then chromatographed over a Sepharose™ Cl-6B column and was found in those fractions with proteins of molecular weights greater than 50,000. Those fractions were then pooled and chromatographed over a cation exchange column SP-Sephadex™ at pH 6.0 and were found to be in the 0–0.2M NaCl wash.

The scar inhibitory factor protein isolate of this invention has been analyzed by both reduced and non-reduced sodium dodecyl sulfate polyacrylamide gel electrophoresis (SDS-PAGE) according to the method of Laemmli disclosed in *Nature* (London) 227: 680–685 (1970) using 10% running gels and 3% stacking gels. Phosphorylase b (97,400), bovine serum albumin (66,200), ovalbumin (45,000), carbonic anhydrase (31,000), soybean trypsin inhibitor (21,500), and lysozyme (14,400), were used as standards. After electrophoresis, gel slabs were fixed and stained for total protein using a colloidal stain as reported by Neuhoff et al in *Electrophoresis* 9: 255–262 (1988) as modified by Integrated Separation Systems™.

FIG. 1 discloses the results of sodium dodecyl sulfate-polyacrylamide gel electrophoresis (SDS-PAGE) of the scar inhibitory factor protein isolate of this invention run under non-reduced (native gel) conditions. Native gels are run using conditions that do not alter either their native (active) three-dimensional configurations or any possible interactions between molecules. The native gel electrophoresis shown in FIG. 1 discloses molecules in their biologically-active, three dimensional configurations. This poses an interesting dilemma when trying to ascertain molecular weights. First, two or more molecules may interact with each other forming a larger entity. Secondly, a linear protein and a globular protein of the same molecular weight may run as separate bands on a native gel. Therefore, molecular weight measurements based on native gels are guesstimations at best.

Figure 2:
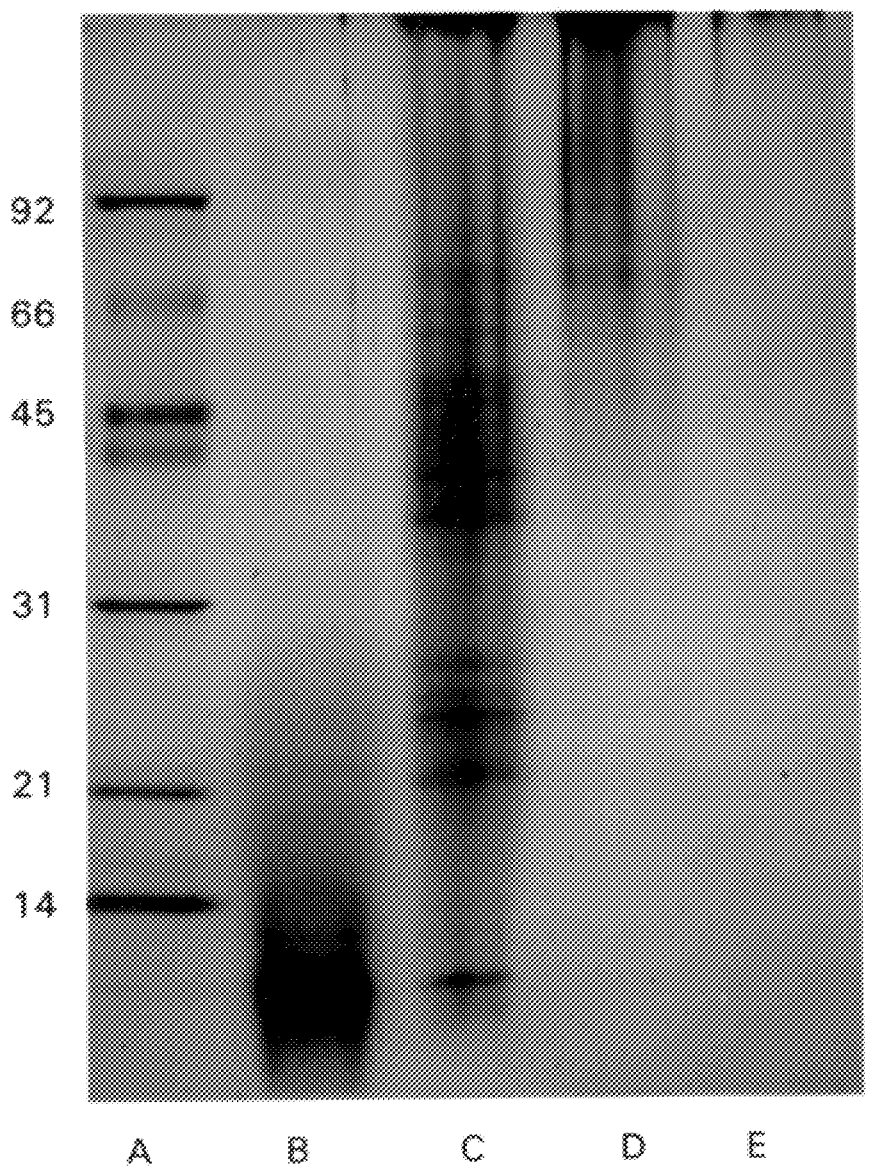
FIG. 2 discloses the results of a sodium dodecyl sulfate-polyacrylamide gel electrophoresis of the scar inhibitory factor protein isolate of this invention run under reduced, denaturating conditions.

Column A of FIG. 1 contains molecular weight standards, phosphorylase b, bovine serum albumin, ovalbumin, carbonic anhydrase, soybean trypsin inhibitor, and lysozyme, run under native, non-reduced conditions (for true molecular weights, see FIG. 2). Columns B–D show gel electrophoresis of the inhibitory factor protein isolate run as 1.0 mg SIF/200 ul sample buffer, 0.100 mg SIF/50 ul sample buffer, and 0.0100 mg SIF/50 ul sample buffer respectively. Five major bands are disclosed at dye front, 16,000, 25,000, 62,500, and stacking gel; three minor bands are shown between 62,500 and the stacking gel, and numerous trace bands are indicated between the dye front and 62,500.

In summary, the electrophoretic results from the non-reduced gel reveal five major bands of material, one band at the dye front, a second band remaining at the stacking gel, and three bands within the running portion of the gel with approximate molecular weights of: 16,000, 25,000, and 62,500; three minor bands between 62,500 and the stacking gel; and numerous trace bands between the dye front and 62,500.

FIG. 2 discloses the gel profile after denaturing agents (boiling, beta-mercaptoethanol, and SDS) were used on the protein bands. The denaturing agents break up native bands into their smallest possible linear structures. The reduced gel shown in FIG. 2 discloses molecules as their smallest possible linear units, usually in a non-biologically-active state.

FIG. 2 discloses the sodium dodecyl sulfate-polyacrylamide gel electrophoresis (SDS-PAGE) of scar inhibitory factor protein isolate run under reduced, denaturating conditions. The numbers at the left of column A are molecular weight standards, i.e., phosphorylase b (97,400), bovine serum albumin (66,200), ovalbumin (45,000), carbonic anhydrase (31,000), soybean trypsin inhibitor (21,500), and lysozyme (14,400) respectively. Columns B–D disclose runs of the scar inhibitory factor protein isolate of this invention, run as 2.1 mg SIF/100 ul sample buffer, 0.105 mg SIF/50 ul sample buffer, and 0.0105 mg SIF/50 ul sample buffer respectively. Three major bands at 33,000, 35,000 and 66,000; 11 minor bands between 14,000 and 200,000; and numerous trace bands between 14,000 and 97,000 are shown or indicated.

The usefulness of using native gels is to compare band numbers and position with reduced gels. Usually the reduced gel will show either the same number or more bands than the native gel. If the gel patterns match, both in band number and position, between the native and reduced, then the molecules are active in their linear configuration, may all be separate entities, and may be much easier to purify. As can be appreciated from a comparison of FIGS. 1 and 2, such is not the case with the scar inhibitory factor protein isolate of this invention.

EXAMPLE 3

Effect of SIF on In Vitro Differentiation

Fertilized White Leghorn chick eggs were candled on day 3 and windowed to assess viability (Young et al, *J. Histochem. Cytochem.*, 37: 223–228 (1989a)). On day 11 the embryos were removed from their eggs, decapitated, and their legs (encompassing knee to ankle joint) were removed and placed into sterile Tyrode's™ buffer (Young et al, *Connect. Tiss. Res.*, 17: 99–118 (1988)). The skin was removed from each leg and the muscle and associated soft tissues were finely minced, triturated to disperse the cells, filtered through sterile cheese cloth and then through a 20 um Nitex™ filter to obtain a single cell suspension (Young et al, J. Tiss. Cult. Meth., 13: 275–284 (1991)). Viable cell numbers were estimated by the dye exclusion test: a 100 ul aliquot of cell suspension was mixed with 100 ul of 0.4% trypan blue in sterile Tyrode's™ solution at pH 7.4, and the viable (dye-excluding) cells counted on a hemocytometer. The cells were plated at $2.5 \times 10^6$ cells per 100 mm tissue culture plate and fed daily with Eagle's™ Minimal Essential Medium (MEM) with Earle's Salts (GIBCO, Gaithersburg, Md.), 10% pre-selected horse serum, and 5% stage-specific embryo extract (Young et al, *J. Tiss. Cult. Method.,* 14: 85–92 (1992)). The cultures were incubated at 37° C. in a humidified, 95% air/5% $CO_2$, incubator.

The cultures were maintained until all myogenic lineage-committed cells had formed multinucleated spontaneously contracting myotubes embedded within multiple confluent layers of mononucleated stellate-shaped cells (Young et al, J. Tiss. Cult. Meth., 13: 275–284 (1991)). The mixed cultures were gently trypsinized with 0.05% trypsin in Moscona's:Moscona's-EDTA buffer for 5–10 minutes at ambient temperature to release the cells from the plate (Young et al, J. Tiss. Cult. Meth., 13: 275–284 (1991)). The cell/trypsin suspension was added to one-half digestate volume of horse serum to inhibit further trypsin activity and centrifuged (Young et al, J. Tiss. Cult. Meth., 13: 275–284 (1991)). The supernatant was discarded, the cells were suspended in incomplete Eagle's™ MEM with Earle's salts, sieved through sterile cheese cloth and 20 um Nitex™, and 100 ul aliquot removed for viability testing and cell counting as described above. The mesenchymal stem cells (Young et al, *J. Tiss. Cult. Method.,* 14: 85–92 (1992)) were either processed as described below for testing or cryopreserved in Eagle's MEM with Earle's salts containing 10% pre-selected horse serum, 5% embryo extract, and 7.5% dimethyl sulfoxide as described by Young et al, *J. Tiss. Cult. Meth.,* 13: 275–284 (1991).

Mesenchymal stem cells were tested with a crude cortical bone extract containing muscle morphogenetic protein (MMP) a protein that induces mesenchymal stem cells to commit to a myogenic phenotype, with and without scar inhibitory factor (SIF) to determine the effects of SIF on differentiation capabilities of these cells. Mesenchymal stem cells were plated at $0.1 \times 10^6$ cells per 35 mm dish in medium consisting of Eagle's MEM with Earle's™ salts, 5% embryo extract, and 10% fetal calf serum. Twenty-four hours later the cultures were switched to, and fed daily thereafter with, medium containing 10 ug/ml MMP (a concentration demonstrating maximal myogenic-inducing activity) with and without SIF.

In each experiment, cultures were assayed on days 3 and 6 of treatment. On day 3, each set of four cultures were first scored for their ability to contract, two cultures were returned to the incubator, and the remaining two cultures had their medium removed, rinsed with Tyrode's™ buffer, and fixed in Perfix™ (Fisher Scientific Group, Pittsburgh, Pa.) for 45 seconds. Both cultures were rehydrated to water, one stained with toluidine blue, the other remained unstained, and both made permanent with glycerine jelly.

Both cultures were then assayed for fusion index within each dish, calculated by determining the number of nuclei residing within multinucleated structures divided by the total number of nuclei. Each dish was divided into 36 equal groups (6×6 matrix) and then 6 groups along each diagonal (12 groups total) were counted and averaged to obtain the fusion index for each plate. On day six the remaining two cultures were removed, assayed for contractility, processed as above for brightfield and phase microscopy, and also assayed for fusion index.

Figure 3A:
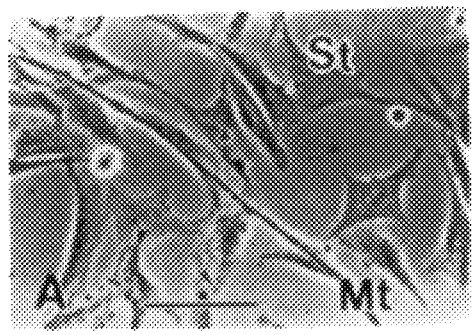
FIG. 3 discloses the results of in vitro experimentation with muscle morphogenetic protein and the scar inhibitory factor protein isolate of this invention.
Figure 3B:

FIGS. 3A–3E show in vitro experimentation with muscle morphogenetic protein (MMP) and scar inhibitory factor (SIF). FIGS. 4B, C and F also show in vitro experimentation with a crude extract containing muscle morphogenetic protein (MMP) and the scar inhibitory factor of this invention (SIF).

Twenty-four hours after the replating discussed above and before treatment started, FIG. 3A shows that the one in vitro culture contained predominantly stellate-shaped cells, approximating in appearance the pluripotent mesenchymal stem cells described by Young et al, *J. Tiss. Cult. Meth.,* 14: 85–92 (1992). The cells labelled MT are myotubes, a contaminant in the culture containing 6–10 nuclei in length. The cells labelled ST are the stellate-shaped, mesenchymal stem cells. The cultures in FIGS. 3A–3E where then fed daily with Eagle's™ MEM with Earle's salts containing 5% embryo extract, 10% fetal calf serum, with or without 10 ug/ml muscle morphogenetic protein (MMP), and with or without 2 ul/ml scar inhibitory factor (SIF).

By the third day of treatment, the control cultures with MMP demonstrated two types of responses. One response shown in FIG. 3B consisted of two morphologically distinct cell types, stellate-shaped cells and spindle-shaped cells (similar in appearance, respectively, to mesenchymal cells and fibroblasts as described by Young et al in 1992. In FIG. 3B, the cells labelled SP are the spindle-shaped (fibroblastic) cells. It is also important to note the absence of any myotubes within the culture.

The second response consisted predominantly of just spindle-shaped cells, similar to that shown in FIG. 4B. FIG. 4B shows cultured mesenchymal stem cells in Eagle's™ MEM containing 10% fetal calf serum and 200 ug/ml lyophilized crude bone extract containing MMP. A few myotubes were also found to be present.

Figure 3C:
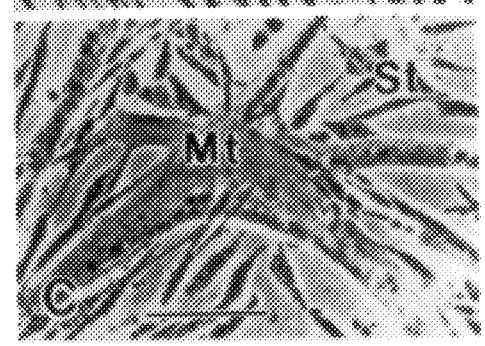
Figure 4A:
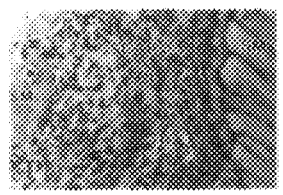
FIG. 4 discloses the results of in vitro and in vivo experimentation with a crude extract, muscle morphogenetic protein and the scar inhibitory factor protein isolate of this invention.
Figure 4B:
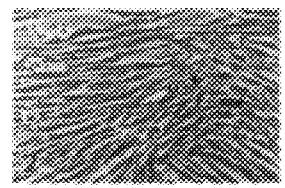
Figure 4C:
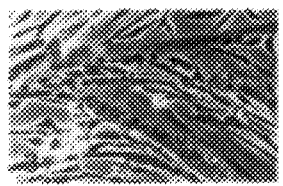

The experimental cultures incubated with medium containing MMP and SIF shown in FIGS. 3C and 4C displayed varying quantities of stellate-shaped cells and large branched multinucleated structures, similar in appearance to myotubes as described by Young et al in 1992. One will note that the difference between FIG. 3B and 3C is the fact that the culture of FIG. 3C also includes SIF. Similarly the only difference between FIG. 4B and 4C is the presence in the culture of FIG. 4C of SIF. Incubation in Eagle's™ MEM containing 10% fetal calf serum with SIF alone (without MMP), demonstrated predominantly stellate-shaped cell-containing cultures as shown in FIG. 4F.

Figure 3D:
Figure 3E:
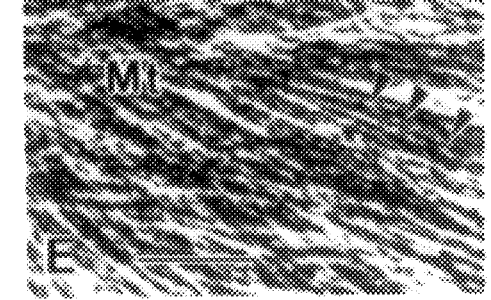

After six days of treatment, both control and experimental cultures displayed confluent cell layers. FIG. 3D discloses that the control cultures contained mononucleated spindle-shaped, fibroblastic cells demonstrating swirl patterns and having a fusion index of less than 1% myotubes are present. Meanwhile, FIG. 3E discloses that experimental cultures displayed linear and branched multinucleated structures that spontaneously contracted and demonstrated a 95% fusion index. The arrowheads point to centrally located nuclei. Once gain, the difference between FIGS. 3D and 3E is the fact that the culture of FIG. 3E includes SIF, and consequently the fibroblastic cells are noticeably absent.

EXAMPLE 4
Effects of SIF on In Vivo Differentiation

FIGS. 4A, D–E, and G–H disclose the results of in vivo experimentation with a crude extract containing muscle morphogenetic protein (MMP) and scar inhibitory factor (SIF).

Implant material was prepared by mixing proteins with two separate controlled-release vehicles: atelo typed-I collagen and bioerodible, surface eroding polymer matrix. Twenty milligrams of dry weight protein was mixed 1:1 with 20 mg of atelo type-I collagen supplied as a 3 mg/ml solution in 0.01N HCl (Vitrogen™, Collagen Corporation, Palo Alto, Calif.) and adding 1.5 ml of 8M Gdn-HCl to yield a final concentration of 2.7M Gdn-HCl. The solution was transferred to a dialysis bag and dialyzed five times against distilled water at 4° C. (1:100 ratio), then three times against 95% ethanol. The solution was then lyophilized in a sterile container prior to implantation.

A bioerodible, surface-eroding polymer matrix controlled-release delivery vehicle having the implant proteins interspersed throughout the matrix was prepared as described in U.S. patent application Ser. No. 742,264 to Laurencin et al, filed Aug. 7, 1991, which patent application is incorporated herein by reference.

Implant proteins consisted of 20 mg dry weight of bovine serum albumin (BSA-control), 20 mg of lyophilized muscle morphogenetic protein (MMP-exp), and 20 mg of a lyophilized mixture of muscle morphogenetic protein and scar inhibitory factor (MMP/SIF-exp).

Breeding-age adult male mice were anesthetized by Metophane™ inhalation, the operational area was swabbed with 70% ethanol, and a small incision made in the skin. For the intramuscular pouch, a small pouch in the back of the thigh musculature (semimembranosus, semitendinosus muscles and biceps femoris) was created by blunt dissection.

No delivery vehicle (control), delivery vehicle only (control), BSA-control, MMP-exp, or MMP/SIF-exp was implanted within the intramuscular pouch and the skin stapled closed. The mice were placed under a heat lamp, containing a incandescent light bulb, during postoperative recovery to maintain body heat and returned to their respective cages.

At tissue harvest, mice were euthanized with ether, staples removed, and the implant area plus 2–4 mm of surrounding tissue was removed for histological analysis. The tissues were fixed in 10% neutral buffered formalin, water washed, and processed for Paraplast embedment and serial sectioning at 5 um as described by Young et al, *Anat. Rec.,* 212: 183–194 (1985).

Alternate slides containing tissue sections were stained in either toluidine blue as described by Young et al, *J. Morph.,* 210: 89–103 (1989) and assayed for early stage myogenic profiles within the implant, within the connective tissue scar immediately adjacent to and surrounding the implant, and along the interface between newly formed scar tissue and the transected adult skeletal muscle tissue. Early stage myogenic profiles were characterized by the presence of multinucleated myotubes and/or small diameter myofibers with centrally located nuclei as described in the preceding Young et al reference.

Histological analysis of the control implants, composed of no vehicle-controls, vehicle-controls, and BSA-controls, demonstrated a dense interwoven connective tissue scar within and surrounding the area of the implant as shown in FIG. 4A. Small regenerating myofibers were present only immediately adjacent to the scar: adult muscle interface.

FIG. 4A shows a sample of tissue taken on the ninth day after implantation of a type-I collagen-based controlled release delivery vehicle containing purified bovine serum albumin (species matched substance) control into an intramuscular pouch within the soleus muscle of a 5–8 week old sibling CBF-1 male mouse. The label SM denotes skeletal muscle, while the asterisk denotes a connective tissue scar.

Figure 4D:
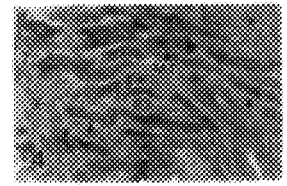
Figure 4E:
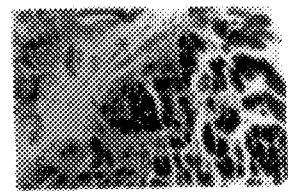
Figure 4F:
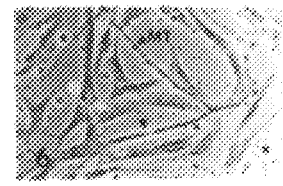

Analysis of the MMP-exp as shown in FIGS. 4D and 4E revealed myogenic profiles embedded within the confines of the connective tissue scar in connection with both a collagen-based delivery vehicle and as polymer-based delivery vehicle. Small regenerating myofibers were also present along the scar: adult muscle interface.

FIG. 4D shows a sample of tissue taken on the ninth day after implantation of a type-I collagen-based controlled release delivery vehicle containing a crude bone extract with MMP into an intramuscular pouch within the soleus muscle of a 5–8 week old sibling CBF-1 male mouse. The label MT denotes myotubes embedded in a connective tissue scar. The difference between the results associated with FIG. 4D compared with FIG. 4A is the fact that the sample shown in FIG. 4D includes MMP.

FIG. 4E shows a sample of tissue taken on the ninth day after implantation of a polyanhydride controlled release delivery vehicle containing a crude bone extract including MMP into an intramuscular pouch under conditions similar to those discussed with respect to FIG. 4D. The label RM denotes regenerating myotubes having centrally located nuclei. The asterisks denote connective tissue scar. The label P denotes the remnants of the polyanhydride delivery vehicle.

Analysis of the MMP/SIF-exp revealed a thin connective tissue scar enclosing intact regenerating muscles, each surrounded by normal structural epimysial connective tissue. Small regenerating myofibers were also present along the scar: adult muscle interface. Each regenerating muscle was composed of multiple muscle fascicles surrounded by normal structural perimysial connective tissue. And each fascicle was composed of individual myofibers with centrally located nuclei surrounded by normal structural endomysial connective tissue. These regeneration morphologies occurred for both the collagen-based and polymer-based delivery vehicles shown in FIGS. 4G and 4H respectively.

Figure 4G:
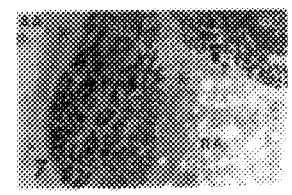
Figure 4H:
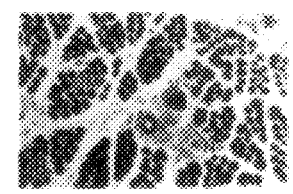

FIGS. 4G and 4H show the same delivery vehicles as FIGS. 4D and 4E respectively, but also include the SIF of this invention. The label SM in FIG. 4G denotes skeletal muscle fibers with peripherally located nuclei. The label RM in both FIGS. 4G and 4H denotes regenerating myotubes with centrally located nuclei. Similarly, the asterisks in both denote connective tissue scar. In FIG. 4G, the label AA denotes adult adipose tissue. In FIG. 4H, the labels V, A and N denote vein, artery and nerve bundle respectively.

Significantly, the regenerating muscles seen in FIG. 4H with the polymer-based delivery vehicle plus MMP and SIF also disclose an intact neurovascular triad (vein, artery, and nerve) within the regenerating muscle. The presence of the neurovascular triad suggest the potential for restoration of physiological function by that regenerating muscle.

In summary, the results shown in FIGS. 3A–3E clearly demonstrate the dramatic differences between cultured mesenchymal stem cells treated with a muscle-inducing agent both with and without the presence of SIF. By treating the cultures only with MMP, the end result is fibroblastic-like cells as shown in FIGS. 3B and 3D. However, most significantly, treating the culture with SIF results in the cells differentiating into muscle cells as shown in FIGS. 3C and 3E.

Furthermore, the results shown in FIGS. 4A–4H also dramatically demonstrate the differences between cultured mesenchymal cells and the cells of living animals treated with and without SIF. In vivo treatment without MMP and SIF results in scar tissue as shown in FIG. 4A. Similarly, FIG. 4B shows that in vitro treatment with only MMP results in fibroblasts. However, FIG. 4C exhibits an absence of scarring.

Continuing, FIG. 4D shows in vivo treatment with MMP, but without SIF, results in myotubes embedded within connective tissue scar. Further, FIG. 4F shows that in vitro treatment only with SIF results in retention of the mesenchymal stem cell appearance, but without any differentiation. Finally, FIGS. 4G and 4H show the results of in vivo treatment with both MMP and SIF. The results disclose intact regenerating muscle bundles.

The results of the experiments associated with the composition and method of this invention demonstrate that the composition and method of the invention selectively inhibits stem cell fibroblastic lineage commitment and differentiation into scar-connective/tissue structures both in vitro and in vivo. While the scar inhibitory factor herein described and its method of use constitutes the preferred embodiment of this invention, it is to be understood that the invention is not limited to this precise composition or method and that changes may be made therein without departing from the scope of the invention which is defined in the appended claims.

What is claimed is:

1. Purified pluripotent mesenchymal stem cells, which cells are substantially free of multinucleated myogenic lineage-committed cells, and which cells are predominantly stellate-shaped cells, wherein the mesenchymal stem cells form predominantly fibroblastic cells when contacted with muscle morphogenic protein in tissue culture medium containing 10% fetal calf serum and form predominantly branched multinucleated structures that spontaneously contract when contacted with muscle morphogenic protein and scar inhibitory factor in tissue culture with medium containing 10% fetal calf serum.

2. The pluripotent mesenchymal stem cells of claim 1 isolated from muscle.

3. The pluripotent mesenchymal stem cells of claim 2 isolated from chick muscle.

4. Purified pluripotent mesenchymal stem cells prepared by the method comprising:
   a) preparing a single cells suspension of muscle cells;
   b) culturing the cells in culture medium supplemented with (i) 10% preselected serum or (ii) 10% horse serum or fetal bovine serum supplemented with an effective amount of scar inhibitory factor at 37° C. in a humidified $CO_2$ incubator until myogenic lineage-committed cells form multinucleated spontaneously contracting myotubes embedded within multiple confluent layers of mononucleated stellate-shaped cells;
   c) releasing the cells from the plate; and
   d) separating the mesenchymal stem cells from the multinucleated cells.

5. The pluripotent mesenchymal stem cells of claim 4, which have been cryopreserved in cell culture medium containing (i) 10% pre-selected serum or (ii) 10% horse serum or fetal bovine serum supplemented with an effective amount of scar inhibitory factor, and 7.5% dimethyl sulfoxide.

6. The pluripotent mesenchymal stem cells of claim 4 wherein the pre-selected serum is pre-selected horse serum.

7. The pluripotent mesenchymal stem cells of claim 4 isolated from muscle.

8. The pluripotent mesenchymal stem cells of claim 7 isolated from chick muscle.

9. The pluripotent mesenchymal stem cells of claim 8 wherein the culture medium further comprises about 5% stage-specific embryo extract.

10. The pluripotent mesenchymal stem cells of claim 4 which are released by trypsin treatment.

11. A method for obtaining purified pluripotent mesenchymal stem cells comprising:
    a) preparing a single cells suspension of muscle cells;
    b) culturing the cells in culture medium supplemented with (i) 10% pre-selected serum or (ii) 10% horse serum or fetal bovine serum supplemented with an effective amount of scar inhibitory factor at 37° C. in a humidified $CO_2$ incubator until myogenic lineage-committed cells had formed multinucleated spontaneously contracting myotubes embedded within multiple confluent layers of mononucleated stellate-shaped cells;
    c) releasing the cells from the plate; and
    d) separating the mesenchymal stem cells from the multinucleated cells.

12. The method according to claim 11, further comprising cryopreserving the pluripotent mesenchymal stem cells in cell culture medium containing (i) 10% pre-selected serum or (ii) 10% horse serum or fetal bovine serum supplemented with an effective amount of scar inhibitory factor, and 7.5% dimethyl sulfoxide.

13. The method according to claim 11 wherein the pre-selected serum is pre-selected horse serum.

14. The method according to claim 11 wherein the pluripotent mesenchymal stem cells are isolated from muscle.

15. The method according to claim 14 wherein the pluripotent mesenchymal stem cells are isolated from chick muscle.

16. The method according to claim 15 wherein the culture medium further comprises about 5% stage-specific embryo extract.

17. The method according to claim 11 wherein the pluripotent mesenchymal stem cells are released by trypsin treatment.

* * * * *